United States Patent
Kuroshima et al.

(10) Patent No.: US 7,824,608 B2
(45) Date of Patent: Nov. 2, 2010

(54) METHOD FOR DEWATERING ENDOSCOPE CHANNELS

(75) Inventors: Hisashi Kuroshima, Tokyo (JP); Akio Ogawa, Tokyo (JP); Kojiro Kotani, Tokyo (JP); Takayoshi Iwanami, Tokyo (JP); Hideto Onishi, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 897 days.

(21) Appl. No.: 11/701,846

(22) Filed: Feb. 2, 2007

(65) Prior Publication Data

US 2007/0193605 A1    Aug. 23, 2007

(30) Foreign Application Priority Data

Feb. 2, 2006   (JP)  .............................. 2006-026235

(51) Int. Cl.
*A61L 2/18* (2006.01)
(52) U.S. Cl. ..................... 422/28; 422/105; 134/22.11
(58) Field of Classification Search .................. 422/28, 422/33, 105; 134/22.11
See application file for complete search history.

(56) References Cited

U.S. PATENT DOCUMENTS 5,749,829 A * 5/1998 Yokoi et al. ................. 600/153

6,797,245 B2 * 9/2004 Nakanishi et al. ........... 422/300

FOREIGN PATENT DOCUMENTS

| DE | 3835861 A | * | 4/1990 |
| JP | 2003-111725 | | 4/2003 |

OTHER PUBLICATIONS

Derwent Abstract of DE 3835861 A; Inventor: Ennen et al.*

* cited by examiner

*Primary Examiner*—Sean E Conley
(74) *Attorney, Agent, or Firm*—Scully, Scott, Murphy & Presser, P.C.

(57) ABSTRACT

An apparatus washes/disinfects, at a time, a plurality of endoscopes having a plurality of channels with different diameters, and dewaters the channels at a time. For the dewatering, the apparatus includes plural ports for receiving air supply, and a plurality of tubes for connecting between each of the plurality of ports and each of the plurality of channels in each of the plurality of endoscopes. The apparatus also includes an on-off valve for intermittently supply air to the ports, and a control unit for opening/closing the valve a plurality of times at a predetermined ratio. Water droplets remaining in a large-diameter channel are mainly moved by wind pressure of continuously flowing air while the valve is open, and discharged. Water droplets in a smaller-diameter channel are mainly moved by hammer effect of high-pressure air caused while the valve is closed, and discharged. The valve opening/closing is repeated for complete dewatering.

5 Claims, 23 Drawing Sheets

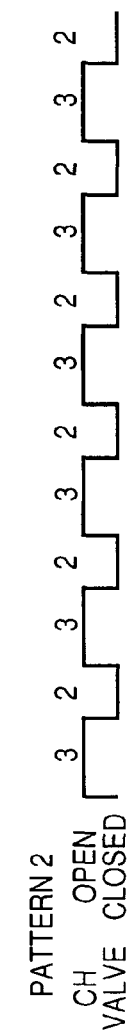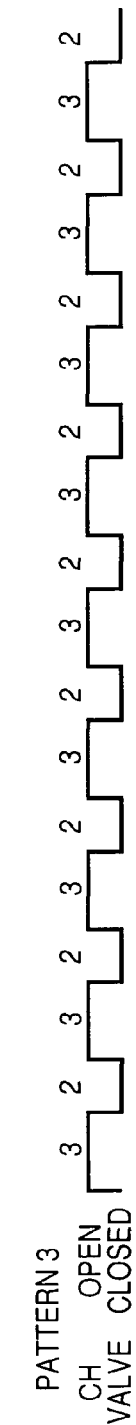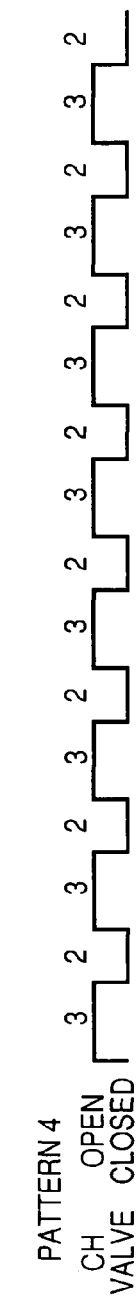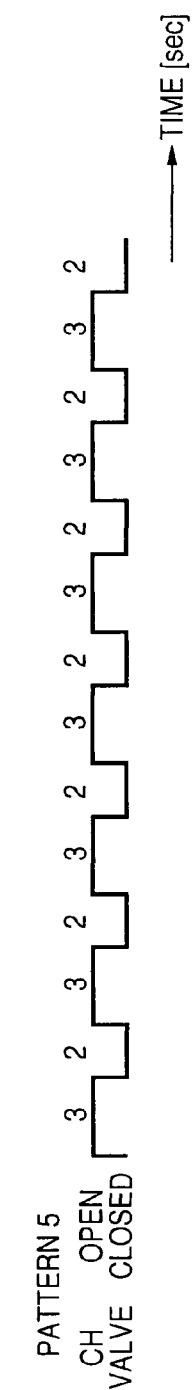
FIG. 5A (PRIOR ART) PATTERN 1
FIG. 5B PATTERN 2
FIG. 5C PATTERN 3
FIG. 5D PATTERN 4
FIG. 5E PATTERN 5

FIG. 6

| SCOPE | CHANNEL/ PATTERN | AMOUNT OF REMAINING WATER AFTER AIR SUPPLY BASED ON THE FIVE PATTERNS | | | | |
|---|---|---|---|---|---|---|
| | | 1 | 2 | 3 | 4 | 5 |
| FIRST ENDOSCOPE | AW 101 (SMALL DIAM.) | 4 | 3.4 | 3 | 2.4 | 1.3 |
| | S102 (LARGE DIAM.) | 0.7 | 0.4 | 0.3 | 0.3 | 0.3 |
| | SUM TOTAL | 4.7 | 3.8 | 1.9 | 2.7 | 1.6 |
| SECOND ENDOSCOPE | AW 111 (SMALL DIAM.) | 3 | 3.2 | 2.3 | 3 | 3 |
| | S112 (LARGE DIAM.) | 1.1 | 0.5 | 0.3 | 0.5 | 0.3 |
| | SUM TOTAL | 4.1 | 3.7 | 2.6 | 3.5 | 3.3 |

METHOD FOR DEWATERING ENDOSCOPE CHANNELS

CROSS REFERENCES TO RELATED APPLICATIONS

This application is based on and claims the benefit of priority from earlier Japanese Patent Application No. 2006-026235 filed Feb. 2, 2006 the description of which is incorporated herein by reference.

BACKGROUND OF THE INVENTION 1. (Field of the Invention)

The present invention relates to an apparatus and method for dewatering channels (or ducts) of an endoscope used such as for medical purposes, after disinfecting and washing the channels. In particular, the present invention relates to an apparatus and method for dewatering channels by moving water droplets with a pressure of air supplied into the channels, so as to be discharged from outlets of the individual channels.

2. (Related Art)

In examining and treating a body cavity of an object to be examined, endoscopic therapy using an endoscope apparatus is now an indispensable modality. Use of an endoscope apparatus for such an examination and treatment involves attachment of garbage not only to an outer surface of an insert part of an endoscope to be inserted into a body cavity, but also to endoscope channels, such as an air-water supply channel (hereinafter referred to as an "AW channel") formed inside the insert part or a manipulation tool insertion channel that also serves as a suction channel (hereinafter referred to as an "S channel"). Therefore, a used endoscope requires, without fail, washing/disinfection not only for its outer surface but also for the interior of each of the channels.

Generally, when performing washing/disinfection of an endoscope using a washing/disinfecting apparatus, a used endoscope is accommodated and set in a washing/disinfecting vessel of the washing/disinfecting apparatus first.

Then, a channel connector port of the endoscope channel, which is opened in an outer surface of the endoscope to wash/disinfect the interior of the endoscope channel is connected, through a tube, for example, to a port provided in the washing/disinfecting vessel, which port supplies fluid, such as liquid or gas, into the endoscope.

For example, a channel connector port of the AW channel of the endoscope is connected to a first port of the washing/disinfecting vessel through a first washing tube. Similarly, a channel connector port of the S channel of the endoscope is connected to a second port of the washing/disinfecting vessel through a second washing tube.

Then, after closing a cover of the washing/disinfecting vessel, a starting switch is turned on. Then, a washing step is started, first, based on a washing/disinfecting program imparted in advance to the washing/disinfecting apparatus, which is then followed by a disinfecting step, in the washing step, washing liquid is supplied into the washing/disinfecting vessel first. When the washing liquid has reached a predetermined level, washing is started. The washing liquid is circulated so that the outer surface of the endoscope is washed by the stream.

In this case, the washing liquid in the washing/disinfecting vessel that has been sucked by a circulating pump is alternately discharged from the first port and the second port with the aid of an on-off valve, whereby the washing liquid is introduced through the individual tubes and the individual channel connector ports into the AW channel and the S channel. It will be appreciated that, by turning a switch, the washing liquid may be simultaneously discharged from the first and the second ports. In this way, the interiors of the AW channel and the S channel are washed by the introduced washing liquid.

After finishing the washing step, disinfecting liquid is supplied, at the subsequent disinfecting step, into the AW channel and the S channel in the same way as in supplying the washing liquid to perform disinfection of the outer surface of the endoscope and the interiors of the channels. Then, rinsing water is supplied in the same way again as in supplying the washing liquid to rinse the outer surface of the endoscope and the interiors of the channels.

Finally, at a drying step, in the same manner as in supplying the washing liquid and the disinfecting liquid, high-pressure air is supplied into the AW channel and the S channel for a predetermined period of time, (e.g., 15 seconds) by using an air supply apparatus, such as a compressor, so as to accelerate removing water (called "dewatering," i.e. removing water droplets by moving them with the wind force of air for discharge from the outlets of the individual channels) as well as drying of the interiors of the individual channels in the endoscope, for completion of the series of steps. It will be appreciated that even in the case where the endoscope is provided with a front water-supply channel, for example, the interior of the front water-supply channel can be washed, disinfected and dried in the same manner as explained above.

The endoscope washing/disinfecting apparatus which can wash/disinfect the interiors of the channels as well as the outer surface of the endoscope, as described above, is well known as described in Japanese Patent Laid-open No. 2003-111725, for example.

When air is simultaneously discharged from a plurality of ports after performing washing/disinfection to dewater the channels having different diameter, a smaller-diameter channel may suffer from difficulty in dewatering due to its so much the larger channel resistance. The endoscope washing/disinfecting apparatus described in Japanese Patent Laid-open No. 2003-111725 takes a measure for this difficulty. In particular, the endoscope washing/disinfecting apparatus disclosed in this patent document is so arranged that a fine hole is formed in the washing tube connecting between the port and the connector port of the small-diameter channel in light of the above difficulty, so that the small-diameter channel can be efficiently dewatered by removing water therefrom in short time through the fine hole in the washing tube.

In order to achieve good efficiency at the steps of washing and disinfecting the endoscope, there is a demand, recently, for an endoscope washing/disinfecting apparatus which enables simultaneous washing/disinfection of two endoscopes. In this case, as a matter of course, the interiors of the two endoscopes have also to be completely washed/disinfected.

SUMMARY OF THE INVENTION

The present invention has been made in view of the problem described above, and has as its object to provide a dewatering apparatus, a dewatering method, and an endoscope washing/disinfecting apparatus, by which the channels of a plurality of (e.g., two) endoscopes can be simultaneously dewatered. Particularly, the present invention has an object of providing the above apparatus and method for simultaneously and reliably performing dewatering to remove water droplets that remain, after washing/disinfection, in a plurality of different-diameter channels in each of a plurality of endoscopes, in shorter time, to finally dry these channels.

In order to achieve the object provided above, an endoscope washing/disinfecting apparatus of the present invention simultaneously washes/disinfects a plurality of endoscopes each having a plurality of channels of different diameter, and then simultaneously dewaters the plurality of channels in the plurality of endoscopes. The apparatus is provided with a plurality of ports for receiving supply of air for the dewatering, a plurality of tubes each of which is connected between each of the plurality of ports and each of the plurality of channels in each of the plurality of endoscopes, an on-off valve capable of intermittently supplying the air to the plurality of ports, and a control unit for opening/closing the on-off valve for a plurality of times at a predetermined ratio.

Further, in order to achieve the above object, a dewatering apparatus is also provided, which washes/disinfects a plurality of endoscopes each having a plurality of channels of different diameter and then simultaneously dewaters the plurality of channels of the plurality of endoscopes. The dewatering apparatus is provided with a plurality of ports for receiving supply of air for the dewatering, a plurality of tubes each of which is connected between each of the plurality of ports and each of the plurality of channels in each of the plurality of endoscopes, an on-off valve capable of intermittently supplying the air to the plurality of ports, and a control unit for opening/closing the on-off valve for a plurality of times at a predetermined ratio.

Furthermore, in order to achieve the above object, a dewatering method is provided for washing/disinfecting a plurality of endoscopes each having a plurality of channels of different diameter and then for simultaneously dewatering the plurality of channels of the plurality of endoscopes. The dewatering method includes a step of continuously supplying high-pressure air for the dewatering to each of the plurality of channels in each of the plurality of endoscopes for a predetermined first period, a step of stopping supply of the air to each of the plurality of channels in each of the plurality of endoscope for a predetermined second period, and a step of repeating a cycle consisting of the supplying step and the stopping step, for a predetermined number of times.

According to the present invention, the channels of different diameter in each of the two endoscopes can be simultaneously and reliably dewatered and dried. In addition, with the apparatus and method of the present invention, increase in the manufacturing cost and time can be prevented.

BRIEF DESCRIPTION OF THE DRAWINGS

In the appended drawings:

FIGS. 5A to 5E are timing diagrams each illustrating a pattern of intermittent opening/closing of a CH electromagnetic valve, which is performed by a control unit illustrated in FIG. 4;

FIG. 6 illustrates a table showing amounts of remnant water in an AW channel and an S channel in each endoscope after drying treatment by the on-off control of the CH electromagnetic valve according to each of the patterns illustrated in FIGS. 5A to 5E;

FIGS. 8A and 8B are illustrations each explaining another example of air supply pattern;

DETAILED DESCRIPTION OF PREFERRED EMBODIMENTS

Various embodiments of the present invention will now be described with reference to the accompanying drawings.

First Embodiment

With reference to FIGS. 1 to 8A and 8B, hereinafter is described a first embodiment of an endoscope washing/disinfecting apparatus embodying a dewatering apparatus and method according to the present invention.

Figure 1:
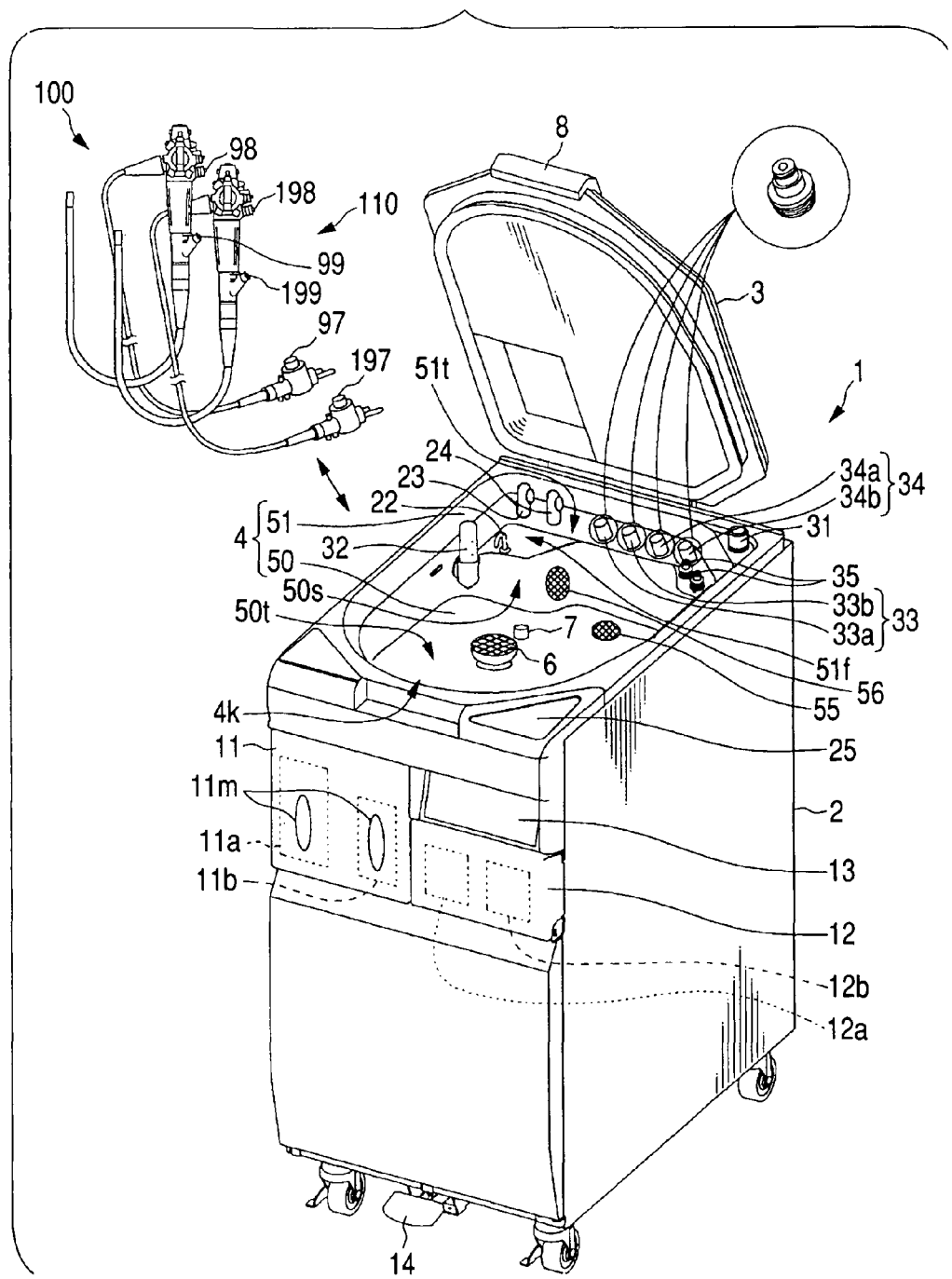
FIG. 1 is a perspective view illustrating an endoscope washing/disinfecting apparatus according to an embodiment of the present invention.

As shown in FIG. 1, an endoscope washing/disinfecting apparatus 1 is an apparatus for washing/disinfecting two used endoscopes all together (hereinafter, the two endoscopes are referred to as a "first endoscope 100" and a "second endoscope 110"). A principal part of the apparatus is made up of a washing apparatus body (hereinafter referred to just as an "apparatus body") 2 and a top cover 3 which is connected to a top portion of the apparatus body 2 through a hinge, not shown, for example, so as to be freely opened and closed.

It will be appreciated that the endoscope washing/disinfecting apparatus 1 may wash/disinfect only one endoscope, i.e. either one of the first endoscope 100 and the second endoscope 110. The present embodiment however will be described taking an example of washing/disinfecting two endoscopes at a time.

The apparatus body 2 and the top cover 3 are so arranged that they are locked together by closing the top cover 3 with a latch 8, for example, which is disposed at a position where the apparatus body 2 and the top cover 3 can face with each other when closed.

At a top portion of a left half, for example, of a front face in FIG. 1 to which an operator of the apparatus body 2 may approach (hereinafter referred to as a "front face"), a detergent/alcohol tray 11 is arranged so as to be drawable frontward of the apparatus body 2.

The detergent/alcohol tray 11 is accommodated with a tank 11a which is filled with a detergent, a liquid used for washing the first endoscope 100 and the second endoscope 110, and a tank 11b which is filled with alcohol, a liquid used for drying the endoscope 100 after being washed/disinfected. Since the detergent/alcohol tray 11 is adapted to be drawable, these liquids can be supplemented to be a predetermined amount.

The detergent filled in the tank 11a is a concentrated detergent which is diluted to a predetermined concentration with tap water that has been filtered by a feed-water filter 17 (see FIG. 4), which will be described later. It will be appreciated that, in the present embodiment, mixture of the detergent and the tap water is referred to as "washing liquid".

The detergent/alcohol tray 11 is provided with windows 11m, through which remnant amounts of the detergent and the alcohol in the tanks 11a and 11b are ensured to be confirmed by an operator.

Further, at a top portion of a right half of the front face of the apparatus body 2, for example, a cassette tray 12 is arranged so as to be drawable frontward of the apparatus body 2. The cassette tray 12 is accommodated with a bottle 12a which is filled with a main agent that will serve as the disinfecting liquid, such as peracetic acid, and used for disinfecting the endoscope 100, and a bottle 12b which is filled with a buffer agent for the main agent. Since the cassette tray 12 is adapted to be drawable, the bottles 12a and 12b are can be supplemented to be a predetermined amount.

Above the cassette tray 12 in the front face of the apparatus body 2, a sub-operation panel 13 is provided in which buttons are arranged, for example, for displaying washing/disinfecting time or instructing warming of the disinfecting liquid.

As shown in FIG. 1, a pedal switch 14 is provided at a bottom of the front face of the apparatus body 2, so that the top cover closed at the top of the apparatus body 2 can be opened upward of the apparatus body 2 by being stepped on by an operator.

Further, as shown in FIG. 1, a main operation panel 25 is provided on the right side of a top face of the apparatus body 2, for example, as seen from the front face to which the operator approaches. In the main operation panel 25, setting switches are arranged, such as a disinfection operation starting switch and a washing/disinfecting mode selection switch.

The apparatus body 2 is also provided, on a rear side of its top face, i.e. near a rear face opposed to the front face, with a feed-water hose connector port 31 to which a feed-water hose 31a connected to a waterline faucet 5 (explained later (see FIG. 4)) is connected, so that tap water can be supplied to the apparatus body 2. The feed-water hose connector port 31 may be provided with a mesh filter for filtering tap water.

Figure 2:
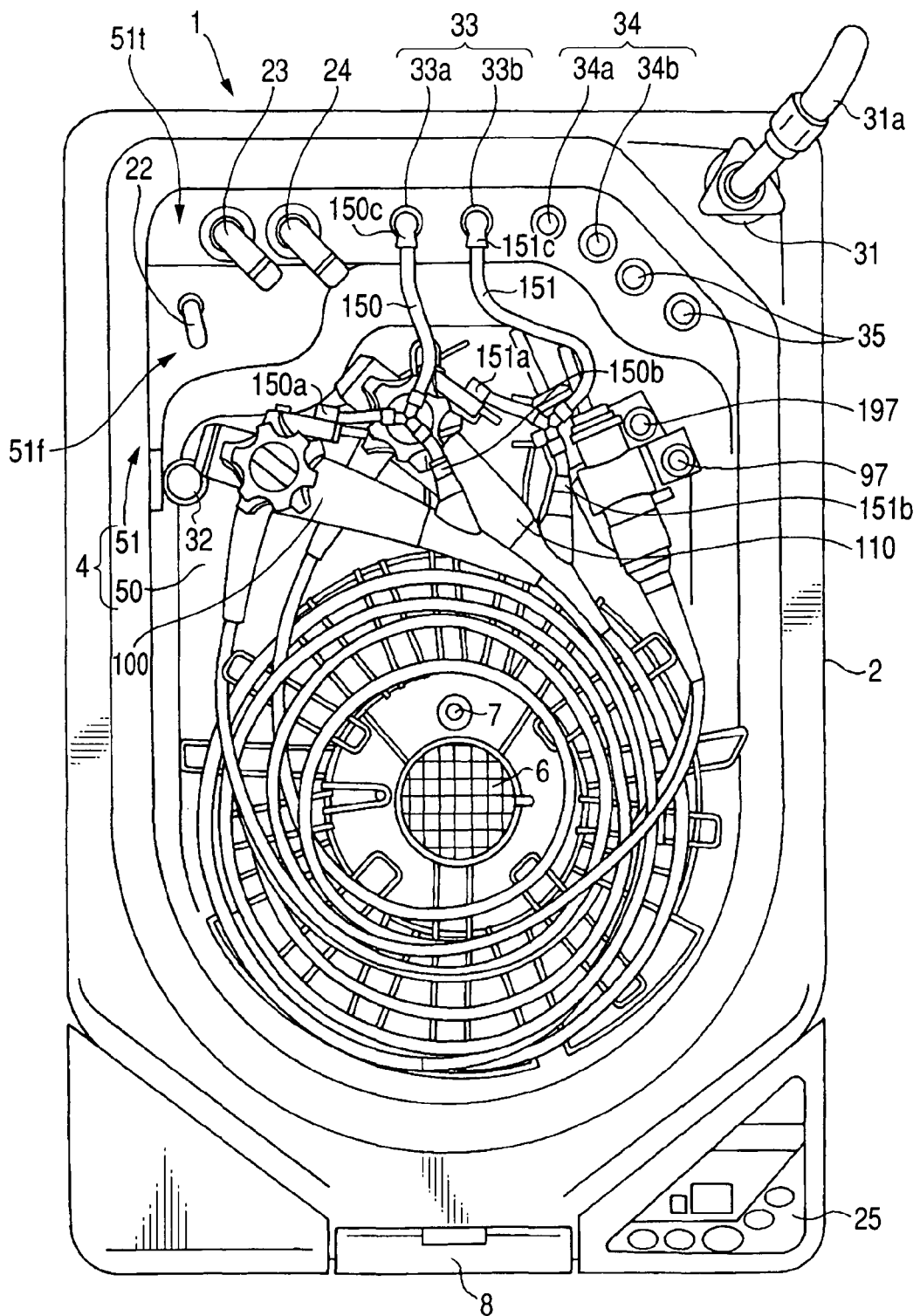
FIG. 2 is a top view of the endoscope washing/disinfecting apparatus with its top cover being opened, in which two endoscopes are accommodated in a washing/disinfecting vessel illustrated in FIG. 1.

Further, as shown in FIG. 2, a washing/disinfecting vessel 4, in which the first endoscope 100 and the second endoscope 110 can be freely accommodated, is provided at substantially a center portion in the top face of the apparatus body 2, being open upward, so as to be opened/closed by the top cover 3. The washing/disinfecting vessel 4 is made up of a vessel body 50 and a terrace 51 which is continuously formed along an outer peripheral edge of an opening of the vessel body 50.

Used first endoscope 100 and the second endoscope 110 can be freely accommodated in the vessel body 50 when they are washed/disinfected. The vessel body 50 is provided with a drain port 55 in its bottom face 50t, so that liquid-fluids, such as the washing liquid, water, and disinfecting liquid, which have been supplied to the vessel body 50 can be drained from the vessel body 50.

A circulator port 56 is provided at an arbitrary position in a peripheral side face 50s of the vessel body 50. The washing liquid, water, disinfecting liquid or the like that have been supplied to the vessel body 50 and those which have been supplied to channels (described later) in the first endoscope 100 and the second endoscope 110 using some means (described later) are circulated being sucked by the circulator port 56 and re-supplied to the vessel body 50 by a feed-water circulation nozzle 24 (described later). The circulator port 56 may be provided with a filter for filtering the washing liquid, water, disinfecting liquid or the like.

The circulator port 56 may be formed in the bottom face 50t of the vessel body 50. In case the circulator port 56 is formed in the bottom face 50t of the vessel body 50, submersion can be accelerated, which may bring forward the timing of supplying the washing liquid, water, disinfecting liquid or the like to the channels of the endoscope 100 or the timing of re-supplying these liquids to the vessel body 50. In addition, formation of the circulator port 56 in the bottom face 50t may bring another advantage that an operator can readily make an approach to the circulator port 56 in changing the filter, for example, provided in the circulator port 56.

A feed-water channel disinfecting port 7 is disposed at substantially the central portion of the bottom face 50t of the vessel body 50 in the washing/disinfecting vessel 4. This port 7 is provided for supplying disinfecting liquid to an internal feed-water channel, not shown, in the endoscope washing/disinfecting apparatus 1 to disinfect the feed-water channel.

Further, a washing case 6 is also disposed at substantially the central portion of the bottom face 50t of the vessel body 50. This washing case 6 is provided for accommodating buttons and forceps stoppers, for example, such as of scope switches for the first and second endoscopes 100 and 110, and for washing/disinfecting these buttons and stoppers or the like together with the first and second endoscopes 100 and 110.

At an arbitrary position in the side face 50s of the vessel body 50, a water-lever sensor 32 with a cover is provided to detect the level of the washing liquid, water, disinfecting liquid or the like supplied to the vessel body 50.

The terrace 51 of the washing/disinfecting vessel 4 has a peripheral terrace face 51t, which is oriented obliquely upward, i.e. inclined by a predetermined angle with respect to the bottom face 50t, for example, of the vessel body 50.

A detergent nozzle 22 is disposed at a face other than the terrace face 51t of the terrace 51, i.e. at a face 51f parallel to the bottom face 50t of the vessel body 50. The detergent nozzle 22 is provided for supplying the washing liquid from the detergent tank 11a to the vessel body 50 through a detergent supply pump 40 (see FIG. 4), which will be explained later. The detergent nozzle 22 may be disposed at the terrace face 51t.

The terrace face 51t of the terrace 51 is provided with a disinfectant nozzle 23 for supplying disinfecting liquid to the vessel body 50 from a chemical liquid tank 58.

The terrace face 51t is also provided with the feed-water circulation nozzle 24 for supplying water used for washing or rinsing to the vessel body 50. The feed-water circulation nozzle 24 also plays a roll of re-supplying the washing liquid, water, disinfecting liquid or the like sucked from the circulator port 56 of the vessel body 50 to the vessel body 50. The disinfectant nozzle 23 and the feed-water circulation nozzle 24 may be disposed at the parallel face 51f.

On the side opposed to an operator's operation position 4k at the terrace face 51t of the terrace 51, there are provided: an air-water-supply/forceps port 33 made up of two ports 33a, 33b for supplying fluid, such as the washing liquid, water, alcohol, disinfecting liquid, air, etc. (hereinafter collectively referred to just as "fluid") to the channels (explained later) provided inside the first and second endoscopes 100 and 110; an auxiliary water-supply/forceps-lifting port 34 made up of two ports 34a, 34b; and two leak detection ports 35. It will be appreciated that the number of the ports 33 to 35 is not limited to the number mentioned above.

The two ports 33a, 33b are adapted to discharge the fluid simultaneously or alternately by a channel electromagnetic valve 28 (hereinafter referred to as "CH electromagnetic valve 28" (see FIGS. 3 and 4)), which will be explained later, serving as the inventive on-off valve.

Figure 3:
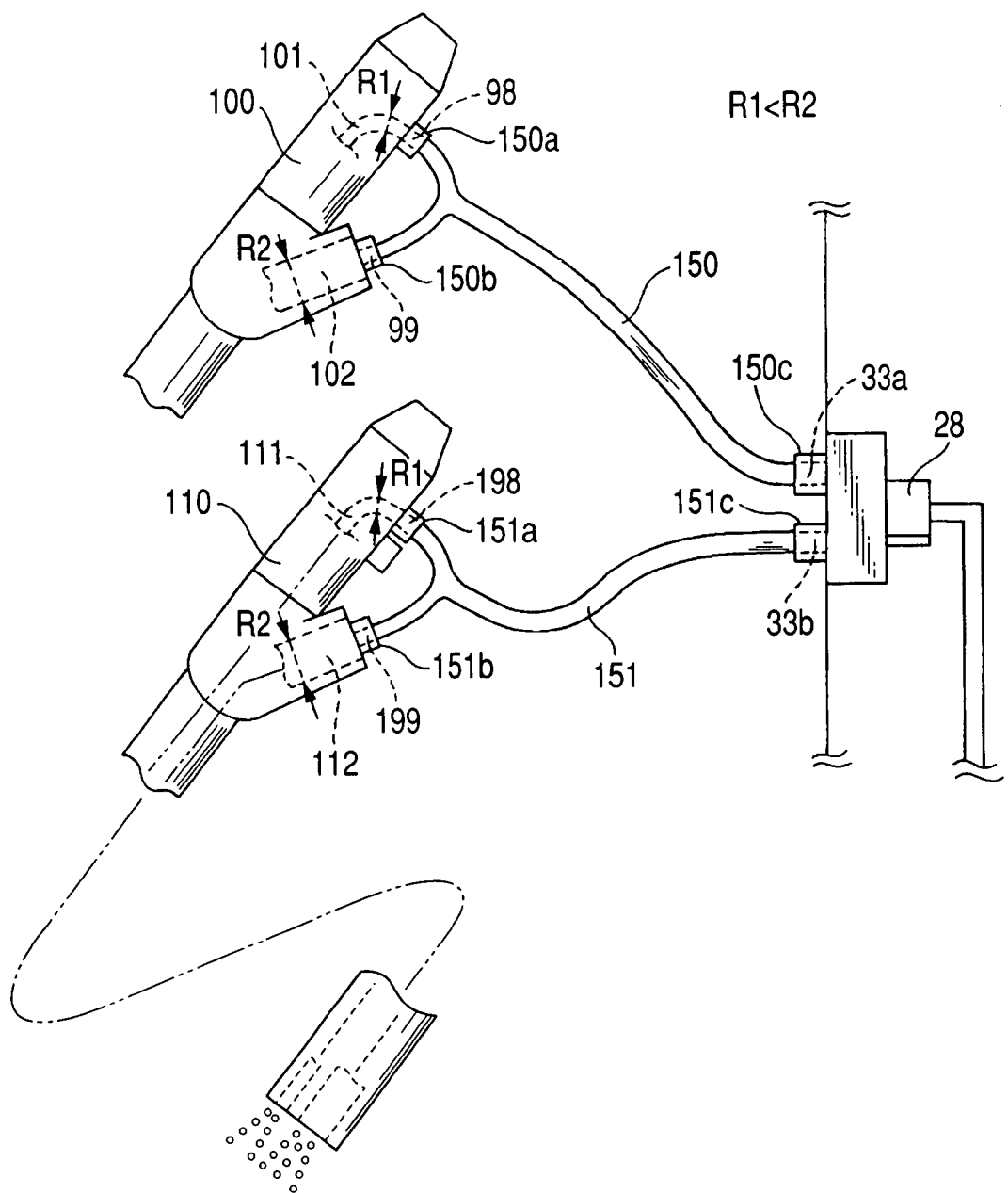
FIG. 3 is a schematic diagram illustrating a state where channel connector ports of each of the two endoscopes illustrated in FIG. 2 are connected to an air-water supply/forceps port through a washing tube.

As shown in FIGS. 2 and 3, in accommodating the used first endoscope 100 in the washing/disinfecting vessel 4, an inflow side connector port 150c of a first branch tube 150 is connected to the air-water-supply/forceps port 33a, a first port. An outflow side of the branch tube 150 is branched into two to have a Y-shaped form, for example.

A first outflow side connector port 150a of the first branch tube 150 is connected to a channel connector port 98 at an outer surface of an air-water supply channel (hereinafter referred to as an "AW channel") 101, or a first channel disposed in the first endoscope 100.

A second outflow side connector port 150b of the first branch tube 150 is connected to a channel connector port 99 at an outer surface of a manipulation tool insertion channel (hereinafter referred to as an "S channel") 102, or a second channel, having a diameter larger than the AW channel (R1<R2) disposed in the first endoscope 100. The manipulation tool insertion channel 102 also serves as a suction channel.

As shown in FIGS. 2 and 3, in accommodating the used second endoscope 110 in the washing/disinfecting vessel 4, an inflow side connector port 151c of a second branch tube 151 is connected to the air-water supply/forceps port 33b, a second port. An outflow side of the branch tube 151 is branched into two to have a Y-shaped form, for example.

A first outflow side connector port 151a of the second branch tube 151 is connected to a channel connector port 198 at an outer surface of an AW channel 111, or a first channel, disposed in the second endoscope 110.

A second outflow side connector port 151b of the second branch tube 151 is connected to a channel connector port 199 at an outer surface of an S channel 112, or a second channel having a diameter larger than the AW cannel 111 (R1<R2) disposed in the second endoscope 110. The S channel 112 also serves as a suction channel.

In case the first and second endoscopes 100 and 110 are each provided with a auxiliary water-supply/forceps-lifting channel, one end of a washing tube, not shown, is connected to a channel connector port of the auxiliary water-supply/forceps-lifting channel of the first endoscope 100 and the other end thereof is connected to the auxiliary water-supply/forceps-lifting port 34a. Similarly, one end of a washing tube, not shown, is connected to a channel connector port of the auxiliary water-supply/forceps-lifting channel of the second endoscope 110 and the other end thereof is connected to the auxiliary water-supply/forceps-lifting port 34b.

As shown in FIG. 2, one end of a washing tube, not shown, is connected to a leak detection connector port 97 of the first endoscope 100 and the other end thereof is connected to one of the two leak detection ports 35. Similarly, one end of a leakage sensing tube, not shown, is connected to a leak detection connector port 197 of the second endoscope 110 and the other end thereof is connected to the other one of the two leak detection ports 35.

Figure 4:
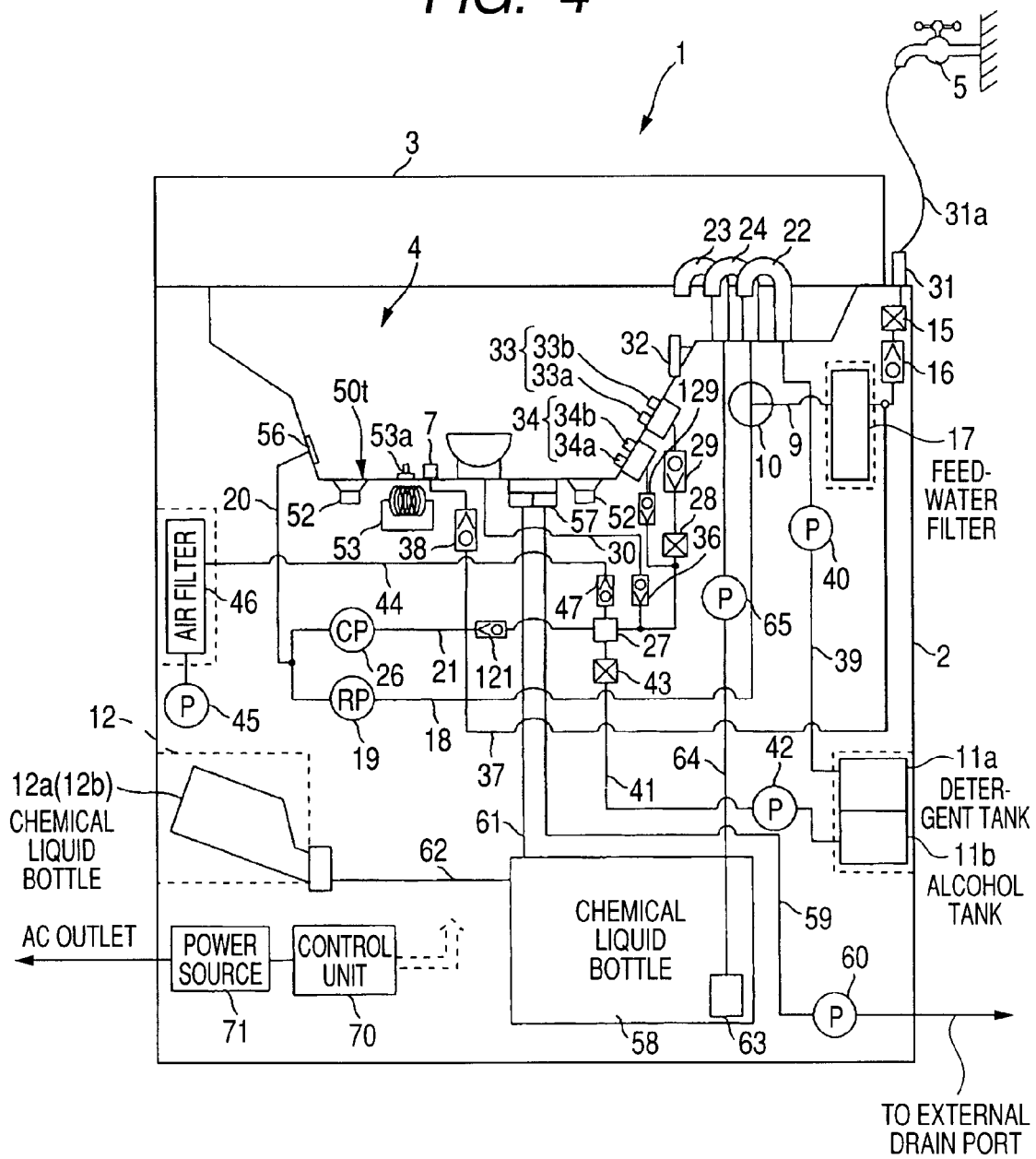
FIG. 4 is an illustration showing an inner configuration of the endoscope washing/disinfecting apparatus illustrated in FIG. 1.

With reference to FIG. 4, hereinafter is described an internal arrangement of the endoscope washing/disinfecting apparatus 1 illustrated in FIG. 1. FIG. 4 illustrates the internal arrangement of the endoscope washing/disinfecting apparatus 1 illustrated in FIG. 1. In the description on the internal arrangement provided hereinafter, explanation on the leak detection ports 35 and circuits or the like communicating with the ports 35 is omitted.

As shown in FIG. 4, in the endoscope washing/disinfecting apparatus 1, the feed-water hose connector port 31 is connected to one end of the feed-water hose 31a whose other end is connected to the external waterline faucet 5, so that tap water can be supplied.

The feed-water hose connector port 31 communicates with one end of a feed-water channel 9. The other end of the feed-water channel 9 is connected to a three-way electromagnetic valve 10. A feed-water electromagnetic valve 15, a check valve 16 and the feed-water filter 17 lie midway in the channel 9 in this order from the side of the feed-water hose connector port 31.

The feed-water filter 17 is made up of a cartridge-type barrier filter so as to be periodically changed. As described above, tap water is removed with foreign matters by passing through the feed-water filter 17.

The three-way electromagnetic valve 10 is connected to one end of a liquid-fluid channel 18 and performs switching operation with its internal valve to attain communication between the feed-water channel 9 and the feed-water circulation nozzle 24 or to attain communication between the feed-water channel 9 and the liquid-fluid channel 18. In other words, the feed-water circulation nozzle 24 communicates with either one of the feed-water channel 9 or the liquid-fluid channel 18 by the switching operation of the three-way electromagnetic valve 10. A liquid-fluid pump 19 is arranged near the other end of the liquid-fluid channel 18.

The circulator port 56 disposed at the washing/disinfecting vessel 4 is connected to one end of a circulation channel 20. The other end of the circulation channel 20 is branched into two so as to communicate with the other end of the liquid-fluid channel 18 and one end of a channel 21.

The other end of the channel 21 communicates with the air-water-supply/forceps ports 33a, 33b and with the auxiliary water-supply/forceps-lifting ports 34a, 34b.

A channel pump 26, a check valve 121, a channel block 27, a CH electromagnetic valve 28 and check valves 29, 129 lie midway in the channel 21 in this order from the side of the one end of the channel 21.

The CH electromagnetic valve 28 supplies liquid-fluid, such as the washing liquid, disinfecting liquid or the like supplied by the channel pump 26 to the air-water-supply/forceps port 33 and the auxiliary water-supply/forceps lifting port 34 in a simultaneous manner, or supplies water only to the auxiliary water-supply/forceps lifting port 34. The CH electromagnetic valve 28 also supplies air supplied by an air pump 45 (explained later) to both of the ports 33 and 34 in a simultaneous manner, or supplies the air only to the port 34.

Specifically, an arrangement is so made that, when the CH electromagnetic valve 28 is open, either the liquid-fluid or air is supplied to the ports 33 and 34, and when the valve 28 is closed, either the liquid-fluid or air is supplied to only the port 34.

The CH electromagnetic valve 28 serves as an inventive on-off valve. The CH electromagnetic valve 28 is adapted to be opened or closed by the on-off control of a control unit 70, which will be described later.

One end of a case channel 30, with the other end being connected to the washing case 6, is connected to the channel 21 at a point between the channel block 27 and the CH electromagnetic valve 28. A relief valve 36 lies midway in the case channel 30.

One end of a disinfection channel 37 is connected to the feed-water channel disinfecting port 7 disposed in the washing/disinfecting vessel 4. The other end of the disinfection channel 37 is connected to the feed-water channel 9 at a point between the feed-water filter 17 and the check valve 16. A check valve 38 lies in the disinfection channel 37 at a point near the feed-water disinfecting port 7.

The detergent nozzle 22 is connected to one end of a detergent channel 39, and the other end of the detergent channel 39 is connected to the detergent tank 11a. The detergent supply pump 40 lies midway in the detergent channel 39.

The alcohol tank 11b is connected to one end of an alcohol channel 41, which is connected to the channel block 27 so as to communicate with the channel 21 in a predetermined manner. In the alcohol channel 41, an alcohol supply pump 42 lies on the side of the alcohol tank 11b, and an electromagnetic valve 43 lies on the side of the channel block 27.

One end of an air channel 44 for supplying air from an air pump 45 made up of a compressor, or an air supply apparatus, for example, is connected to the channel block 27 so as to communicate with the channel 21 in a predetermined manner.

The other end of the air channel 44 is connected to the air pump 45. In the air channel 44, a check valve 47 lies on the side of the channel block 27, and an air filter 46, which is periodically changed, lies on the side of the air pump 45.

A selector valve 57 is disposed at the drain port 55 in the washing/disinfecting vessel 4. With the switching operation of the selector valve 57, the washing liquid or the like is discharged outside, or the disinfecting liquid is re-collected to the chemical liquid tank 58. The selector valve 57 is connected to one end of a drain channel 59 whose other end is connected to a drain hose, not shown, connected to an external drain port for communication therewith. A drain pump 60 is interposed in the drain channel S9. The selector valve 57 is connected to one end of a chemical liquid re-collecting channel 61, and the other end of the channel 61 is connected to the chemical liquid tank 58.

The chemical liquid tank 58 is also connected to one end of a chemical liquid supply channel 62 so that the disinfecting liquid can be supplied thereto. This disinfecting liquid is a mixture of the main agent, such as a disinfectant, filled in the bottle 12a and the buffer agent for buffering the main agent filled in the bottle 12b. The other end of the chemical liquid supply channel 62 is connected to the cassette tray 12 in a predetermined manner.

The chemical liquid tank 58 accommodates therein one end of a chemical liquid channel 64, the end being provided with a suction filter 63. The other end of the chemical liquid channel 64 is connected to the disinfectant nozzle 23 with a chemical liquid pump 65 being interposed midway.

At a rear of the bottom face 50t of the vessel body 50, a plurality of, e.g. two, ultrasonic transducers 52 and a heater 53 are disposed. The number of the ultrasonic transducers is not limited to two. Further, a temperature sensor 53a is provided at substantially the center of the bottom face 50t of the washing/disinfecting vessel 4. The temperature sensor 53a supplies the results of detection to the control unit 70 so that temperature of the heater 53 can be controlled.

The heater 53 plays a roll of warming the disinfecting liquid stored in the washing/disinfecting vessel 4 and circulated inside the apparatus, up to a predetermined temperature. The disinfecting liquid has an optimal temperature at which the disinfecting effects can be exerted the most. The first and second endoscopes 100 and 110 are effectively disinfected by being warmed up to the optimal temperature, I.e. the predetermined temperature.

The temperature sensor 53a detects the temperature of the disinfecting liquid stored in the washing/disinfecting vessel 4 and circulated inside the apparatus and supplies the results of the detection to the control unit 70. The control unit 70 then effects control for driving and stopping the heater 53 based on the results of the detection supplied by the temperature sensor 53a, so that the temperature of the disinfecting liquid can be maintained at the predetermined temperature.

Further, in the endoscope washing/disinfecting apparatus 1, a power source 71 is provided, to which power is supplied from an external AC outlet and to which the control unit 70 is electrically connected. With the supply of various signals from the main operation panel 25 and the sub-operation panel 13 shown in FIG. 1, the control unit 70 effects driving control such as to the pumps and the electromagnetic valves explained above.

In the present embodiment, as will be described hereinafter, the control unit 70 has a function as an on-off valve controller for controlling opening/closing of the CH electromagnetic valve 28 in particular, among the electromagnetic valves explained above. As will be described later, the control unit 70 effects control in such a way that the air that has been supplied to the air-water supply/forceps ports 33a, 33b through the air pump 45 can be intermittently discharged by intermittently opening/closing the CH electromagnetic valve 28, or that the air can be discharged for a predetermined period of time from the air-water supply/forceps ports 33a, 33b by opening the CH electromagnetic valve 28 at preset time.

Since other details of the arrangement of the endoscope washing/disinfecting apparatus 1 are the same as those of the conventional apparatus, the description is omitted herein.

(Effects of the Invention)

Hereinafter are described effects of the endoscope washing/disinfecting apparatus which is arranged as described above. FIGS. 5A to 5E are timing diagrams showing a total of five patterns (air supply patterns) for intermittent on-off control of the CH electromagnetic valve performed by the control unit shown in FIG. 4. FIG. 6 is a table showing the amounts of remnant water in the AW channel and the S channel after drying treatment with the on-off control of the CH electromagnetic valve based on the five patterns shown in FIGS. 5A to 5E.

Washing/disinfecting steps for the first and second endoscopes 100 and 110 in the endoscope washing/disinfecting apparatus 1 are the same as in the conventional washing/disinfecting steps for a single endoscope. Therefore, the description for the washing/disinfecting steps is simplified herein, but focus is made on the description of a drying step for performing dewatering and drying after washing/disinfection.

First of all, the first and second endoscopes 100 and 110 are manually accommodated by an operator into the washing/disinfecting vessel 4 of the washing/disinfecting apparatus 1, as shown in FIG. 2. Thereafter, as shown in FIGS. 2 and 3, the inflow side connector port 150c of the first branch tube 150, whose outflow side are branched into two, is connected to the air-water supply/forceps port 33a.

Then, the first outflow side connector port 150a of the branch tube 150 is manually connected, by the operator, to the channel connector port 98 at the outer surface of an AW channel 101 arranged inside the first endoscope 100. Then, the second outflow side connector port 150b is manually connected, by the operator, to the channel connector port 99 at the outer surface of an S channel 102 arranged inside the first endoscope 100.

Further, the inflow side connector port 151c of the second branch tube 151, whose outflow side is branched into two, is manually connected by the operator to the air-water supply/forceps port 33b. Then, the first outflow side connector port 151a of the second branch tube 151 is connected to the channel connector port 198 at the outer surface of an AW channel 111 arranged inside the second endoscope 110. Similarly, the outflow side connector port 151b is connected to the channel connector port 199 at the outer surface of an S channel 112 arranged inside the second endoscope 110.

After that, the top cover 3 is opened up by the operator from the apparatus body 2, and the starting switch, for example, of the main operation panel 25 described above is operated. In response to the operation, the endoscope washing/disinfecting apparatus 1 automatically operates according to a preset procedure. Thus, both of the first and second endoscopes 100 and 110 including their outer surfaces, the interiors of the AW channels 101, 111 and the S channels 102, 112 are simultaneously washed and disinfected.

In the apparatus 1, the washing/disinfection is followed by simultaneous automatic drying of both of the first and second endoscopes 100 and 110 including the interiors of the AW channels 101, 111 and the S channels 102, 112. In particular, the control unit 70 drives the air pump 45 first. As a result, high-pressure air is supplied to the air-water supply/forceps ports 33a, 33b from the air pump 45 through the air channel 44.

Then, in the state where the high-pressure air is being supplied from the air pump 45, the control unit 70 intermittently performs on-off control of the CH electromagnetic valve 28. In particular, as indicated by a sequence of an air supply pattern 3 of FIG. 5C, the control unit 70 repeatedly (e.g. nine times) controls the CH electromagnetic valve 28 by 3-second opening and 2-second closing. As a matter of course, in case there is no problem in taking longer processing time, the number of repetition may be more than nine.

In this way, air is intermittently supplied through the air-water supply/forceps ports 33a, 33b. The intermittently supplied air is further supplied to the AW channel 101 and the S channel 102 of the first endoscope 100, as well as to the AW channel 111 and the S channel 112 of the second endoscope 110. As a result, water in the AW channels 101, 111 and in the S channels 101, 112 is intermittently moved for dewatering to thereby perform drying treatment. This effect can be exerted in removing alcohol at the time of performing alcohol flush.

The reason why the intermittent control of the CH electromagnetic valve 28 performed by the control unit 70 is 3-second opening and 2-second closing is that the diameter of the AW channels 101, 111 is smaller than that of the S channels 101, 112 (R1<R2). This control is further discussed below in comparison with the conventional sequence.

Executing the conventional sequence will mean to use the sequence of an air supply pattern 1 indicated in FIG. 5A, which has been used for drying a single endoscope. In particular, the air-water supply/forceps ports 33a, 33b are connected to the first and second endoscopes 100 and 110, respectively, to use a sequence for continuously opening the CH electromagnetic valve 28 for 15 seconds as in the sequence for the air supply pattern 1. When air is continuously discharged from the ports 33a, 33b using this sequence, air is mainly supplied to the S channels 101, 112 having larger diameter and smaller channel resistance, while the AW channels having smaller diameter and larger channel resistance are barely supplied with air. Thus, it has been difficult to completely remove droplets that remain in the AW channels 101, 111 after the washing/disinfecting steps (i.e. to move water droplets to the outlet sides of the channels by wind pressure for dewatering).

The unbalanced air supply to the S channels 102, 112 can be seen from the experimental result, as shown in FIG. 6. That is, after drying with the air supply pattern 1, 4-ml water remains in the AW channel 101 while only 0.7-ml water remains in the S channel 102 as for the first endoscope 100. As for the second endoscope 110, 3-ml water remains in the AW channel 111 while only 1.1-ml water remains in the S channel 112.

The experimental result shown in FIG. 6 has been obtained under the conditions that the air pump 45 has a maximum discharge pressure of 0.2 Mpa and a maximum air capacity of 80 L/min (with AC 100V and 50 Hz), and the S channel has a diameter of 3.7 to 4.2 mm, and the AW channel has a diameter of 0.8 to 1.2 m.

Provided that complete drying of the channel interiors is regarded as having been achieved when the remnant water amount in both the AW and S channels becomes 3 ml or less, it is turned out that complete dewatering and drying of the channels cannot be achieved with the air supply pattern 1 for continuously opening the CH electromagnetic valve 28, because, as shown in FIG. 6, the sequence pattern 1 results in 4.7-ml remnant water in the first endoscope 100 and 4.1-ml remnant water in the second endoscope 110.

If the CH electromagnetic valve 28 is opened for more than 15 seconds, the channels can be sufficiently dried. This, however, takes time for the drying step and thus is not preferable. Further, if an air pump with a higher air-supply pressure is used as the air pump 45, the channel interiors can be sufficiently dewatered, which, however, is not preferable again because the manufacturing cost is raised.

The inventors therefore sought for the physical relationship between the shape of water droplets (water) that remain in the channels of the endoscopes after performing washing/disinfection and the length of the diameters of the channels. As a result, the inventors have found a technique of intermittently supplying air as an approach for physical harmonization of the two factors (i.e. the shape and the diameter of each water droplet). This technique will be explained referring to FIGS. 7A and 7B.

Figure 7A:
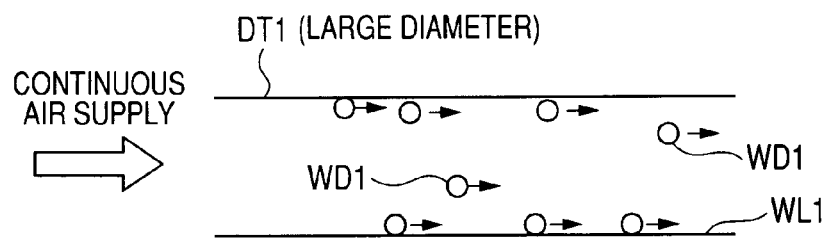
FIGS. 7A and 7B are illustrations of water droplets for explaining their movement in a large-diameter channel and in a small-diameter channel.

As shown in FIG. 7A, in case a diameter of a channel DT1 of an endoscope is large (i.e. the S channels 102, 112), the remnant water droplet WD1 (a diameter of the droplet WD1 is generally smaller than the diameter of such a large channel DT1) in the channel is simply attached to an inner wall WL1 of the channel. Therefore, when air of high pressure, whose level depends on the discharge performance of the air pump 45, is continuously supplied into the channel, the droplet WD1 is pushed by the wind force of the air and moves (or is blown) along the inner wall WL1, and is eventually discharged from an outlet of the channel.

Figure 7B:
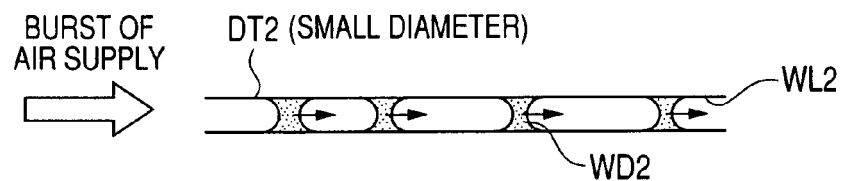

However, it has been revealed that this technique for removing water droplets cannot be applied to a smaller-diameter channel DT2. As shown in FIG. 7B, the smaller-diameter channel DT2 (the AW channels 101, 111) is defined as a channel having a diameter which allows a water droplet WD2 to radially cling to an inner wall WL2 of the channel and to serve as a damper. As to such a damper-shaped droplet WD2, just a continuous air flow of a predetermined pressure cannot move (discharge) or is very unlikely to move the droplet WD2. This is because, the continuous air flow only passes through the damper-shaped droplet WD2 at the center of its diameter and barely allows the peripheral portion of the droplet WD2 clinging to the wall to move with the air pressure.

Thus, in case of the smaller-diameter channel DT2, air hammer effect is required. In order to attain the air hammer effect, the air discharged from the air pump 45 is stocked for a predetermined period in order to raise pressure, and after expiration of the predetermined period, the stocked air is let go at one push for supply. By intermittently providing this hammer effect, the droplet WD2 clinging to the inner wall WL2 of the channel DT2 can be moved along the wall WL2, as shown in FIG. 7B, so that the droplet WD2 can be discharged.

In order to exert the intermittent hammer effect, the CH electromagnetic valve 28 is intermittently opened/closed to intermittently supply air to the pump 45. In other words, by closing the CH electromagnetic valve 28, air is stocked in an intermediate portion of the channel, i.e. between the pump 45 and the valve 28, to raise pressure, and by opening the valve 28, the stocked air is supplied at one push, so that the hammer effect described above can be exerted.

It should be noted that, in the endoscope washing/disinfecting apparatus 1 according to the present embodiment, the smaller- and larger-diameter channels 101, 102 (111, 112) of the endoscopes 100 and 110 are simultaneously dewatered. Thus, the requirements for the air supply to the smaller-diameter channel 101 (111) and the larger-diameter channel 102 (112) have to be satisfied together with the requirements imposed by the entire apparatus. Specifically, all the requirements have to be fulfilled, such as, balancing the need for exerting more hammer effect by the intermittent air supply to the smaller-diameter channel 101 (111) and the need for achieving continuous air supply as long a period as possible to the larger-diameter channel 102 (112); suppressing the entire treatment time to be short; suppressing the discharge performance of the pump 45 to a conventional level; and use of the conventional endoscope washing/disinfecting apparatus for a single endoscope, as it is, for two endoscopes.

In order to find an air supply pattern that meets these requirements, the inventors conducted some experiments. Based on the result of the experiments (see air supply patterns 2 to 5 of FIG. 6), the inventors arrived at the air supply pattern of 3-second opening and 2-second closing for the intermittent control of the CH electromagnetic valve 28 by the control unit 70.

Nine-time intermittent control of the CH electromagnetic valve 28 with 3-second opening and 2-second closing performed by the control unit 70, can sufficiently dry the interiors of the AW channels 101, 111 and the S channels 102, 112 of the first and second endoscopes 100 and 110. This is based on the experimental result, as shown in FIG. 6, that the smaller-diameter channels 101, 111 can be reliably dewatered utilizing the drastic increase of air-supply pressure immediately after opening the CH electromagnetic valve 28 that has been closed up to then.

As indicated by the air supply pattern 3 of FIG. 6, for the first endoscope 100, the remnant water is only 1.9 ml, and for the second endoscope, the remnant water is only 2.6 ml. Since this data well satisfies the limitation of 3 ml or less mentioned above, it is turned out that the sequence pattern 3 sufficiently contributes to dewatering the channels even when two endoscopes are simultaneously subjected to drying and even when the air-supply performance of the air pump 45 is the same as in the case where a single endoscope is dried.

The air supply pattern 3 results in the remnant water of only 1.6 ml for the AW channel 101 of the first endoscope 100 and the remnant water of only 2.3 ml for the AW channel 111 of the second endoscope 110, and thus is also turned out to sufficiently contribute to dewatering the small-diameter AW channels 101, 111.

The reason why the number of the intermittent controls of the valve 28 with 3-second opening and 2-second closing is limited to nine is that, with the six-repetition air supply pattern 2 indicated in FIG. 5B, the remnant water in the first endoscope 100 results in 3.8 ml, and that in the second endoscope 110 results in 3.7 ml as shown in FIG. 6.

As indicated by the air supply pattern 4 of FIG. 5D, in case of eight repetitions, although the remnant water in the first endoscope 100 results in only 2.7 ml, the remnant water in the second endoscope 110 results in 3.5 ml, as shown in FIG. 6. In this case, the latter does not satisfy the 3-ml limitation mentioned above.

As indicated by the air supply pattern 5 of FIG. 5E, in case of seven repetitions, although the remnant water in the first endoscope 100 results in only 1.6 ml, the remnant water in the second endoscope 110 results in 3.3 ml, as shown in FIG. 6. In this case, the latter does not satisfy the 3-ml limitation mentioned above.

For the reasons mentioned above, the control unit 70 has finally been settled down to perform the nine-time intermittent control of the CH electromagnetic valve 28 with 3-second opening and 2-second opening, in dewatering and drying the AW channels 101, 111 and the S channels 102, 112 of the first and second endoscopes 100 and 110.

Use of the finally reached control can provide no less reliable dewatering of the smaller-diameter AW channels 101, 111 than the larger-diameter channels 102, 111 even when the endoscopes 100 and 110 are simultaneously subjected to dewatering. Specifically, as to the S channels 101, 112, they can be dewatered by moving the water droplets with the aid of the pressure of the continuously flowing air during the 3-second opening of the CH electromagnetic valve 28, while, as to the AW channels 101, 111, they can be dewatered by mainly utilizing the hammer effect which is exerted at the time of switching the valve 28 from a closed-state to an open-state. In this way, balanced dewatering effect can be exerted for both of the S channels 101, 112 and the AW channels 101, 111.

As described above, the endoscope washing/disinfecting apparatus of the present invention can reliably and simultaneously dewater and dry two endoscopes each having channels of different diameters, without changing the specification on the number of the air-water supply/forceps ports and on the air pump 45 of the endoscope washing/disinfecting apparatus for a single endoscope, and without increasing cost and treating time.

The advantage mentioned above will now be discussed from a different viewpoint. That is to say, there may be other approaches, as provided below, for coping with the problems of the related art described above. However, the other approaches have both merits and demerits, and thus cannot exert the effects specific to the present embodiment.

One of the approaches may be to simultaneously and continuously discharge high-pressure air into the first and second inflow side ports for a predetermined period of time using an air supply apparatus, such as a compressor, when drying the AW channels and the S channels of the first and second endoscopes with the air supply pattern 1 of FIG. 5A. In this case, the total cross section of the four channels (of the two endoscopes) is larger than that of two channels (of a single endoscope). Since the air supply is performed by a single compressor, the increased cross section may deteriorate the air supply efficiency of the compressor. Thus, it may be difficult to achieve air supply with a pressure required for the dewatering. In addition, since the AW channel, whose diameter is smaller than that of the S channel, has a larger channel resistance than the S channel, the simultaneous air discharge from the first and second ports performed by the on-off valve may allow air supply mainly to the S channels of the two endoscope while hardly allowing air supply to the AW channels. As a result, dewatering of the AW channels is unlikely to be achieved.

Another one of the approaches may be to have only the first inflow side port discharged air by the on-off valve for dewatering of the interiors of the AW channel and the S channel of the first endoscope, and then to have only the second inflow side port discharged air by the on-off valve for dewatering of the interiors of the AW channel and the S channel of the second endoscope, so as to finally dewater the interiors of the AW channels and the S channels of both of the two endoscopes. In this case, however, the separate dewatering of the two endoscopes may increase time of treatment. Still another approach may be to increase time of supplying air. However, in this case as well, the time of treatment is increased.

Another approach may be to again employ simultaneous dewatering of the two endoscopes, in which a compressor with a specification for providing higher air supply pressure than in the case of washing/disinfecting a single endoscope is used to improve the dewatering of the AW channels. In this case, however, the manufacturing cost of the washing/disinfecting apparatus will become higher than the case of manufacturing an apparatus for a single endoscope.

Still another one of the approaches may be, for example, to provide two more inflow side ports in the washing/disinfecting vessel and another on-off valve for performing alternate discharge, and to separately connect the total of four inflow side ports of the washing/disinfecting vessel to the channel connector ports of the AW channels and to the channel connector ports of the S channels of the two endoscopes through four washing tubes, so as to improve dewatering of the AW channels. In this case as well, the manufacturing cost of the washing/disinfecting apparatus will become higher than the case of manufacturing an apparatus for a single endoscope because of the necessity of increasing two ports, two washing tubes and one on-off valve.

Consequently, the endoscope washing/disinfecting apparatus according to the present embodiment can achieve the effects which will not be achieved by the various approaches described above.

In the embodiment described above, nine-time intermittent control has been performed with 3-second opening and 2-second closing of the CH electromagnetic valve 28. However, it will be appreciated that, if time allows, the control can be repeated more than nine times. Further, it will also be appreciated that any intermittent control of the CH electromagnetic valve 28 not limited to 3 and 2 seconds may be used.

It should be noted, however, that in the present invention, the AW channels 101, 111 (smaller-diameter channels) require at least nine-time intermittent air supply and the S channels 102, 112 (larger-diameter channels) require successive air supplies totaling 27 seconds (3×9).

Figure 8B:
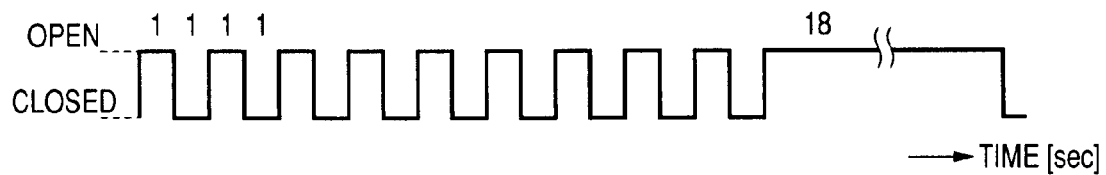
Figure 8B:
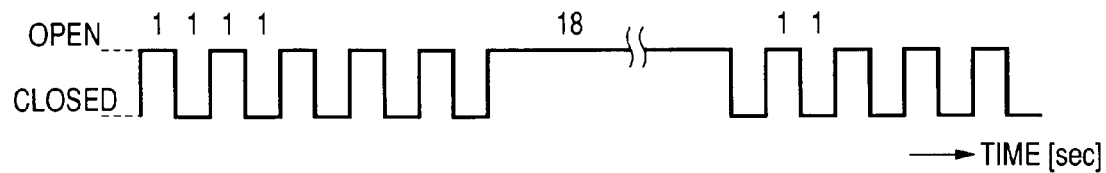

Other air supply patterns for satisfying the above requirements may include one in which a cycle of 1-second valve opening and 1-second valve closing is repeated nine times, and then continuous 18-second valve opening is performed (see FIG. 8A). This pattern can provide nine-time intermittent air supply and continuous 18-second air supply, suppressing the total time of the sequence to 36 seconds. Another pattern may be such that a cycle of 1-second valve opening and 1-second valve closing is repeated five times, then continuous 18-second valve opening is performed, and then a cycle of 1-second valve opening and 1-second valve closing is repeated four times (see FIG. 8B).

Alternatively, the control unit 70 may intermittently effect on-off control of the CH electromagnetic valve 28 to positively dewater the interiors of the AW channels 101, 111 first, and then may open the valve 28 for a predetermined period of, say, 15 seconds to continuously supply high-pressure air to the S channels 102, 112 having smaller channel resistance than the AW channels 101, 111, so that the S channels 102, 112 can be further dewatered.

The number of the endoscopes for the simultaneous washing, disinfecting and drying by dewatering is not limited to two, but may be three or more. In such a case, the same number of ports in the apparatus body and the same number of branch tubes as the number of the endoscopes accommodated in the washing vessel of the apparatus may be made ready.

Second Embodiment

With reference to FIGS. 9 to 14, hereinafter is described an endoscope washing/disinfecting apparatus according to a second embodiment. In the present embodiment and subsequent embodiments, the identical or similar components or processes are given the same references as in the first embodiment for the sake of simplification or omission of explanation.

The present second embodiment is associated with a washing/disinfecting apparatus which can wash, disinfect and dewater individual types of buttons used in the endoscopes.

Figure 9:
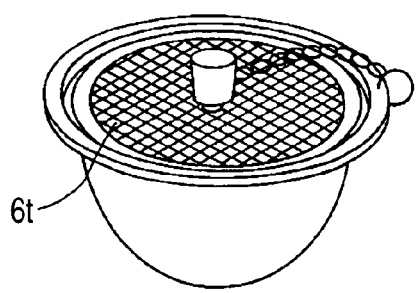
FIG. 9 is an enlarged perspective view of a washing case illustrated in FIG. 1.
Figure 10:
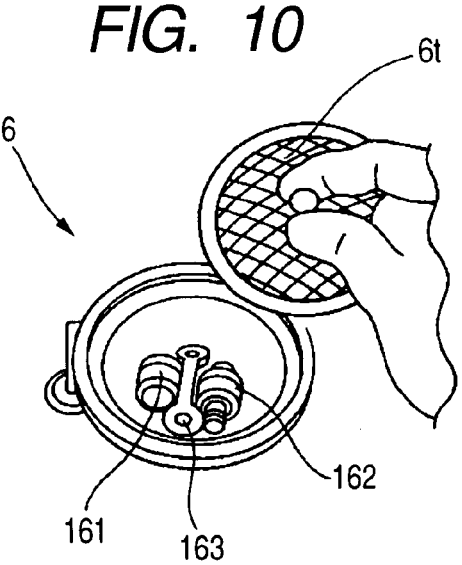
FIG. 10 illustrates a state where a cover of the washing case illustrated in FIG. 9 has been opened.
Figure 11:
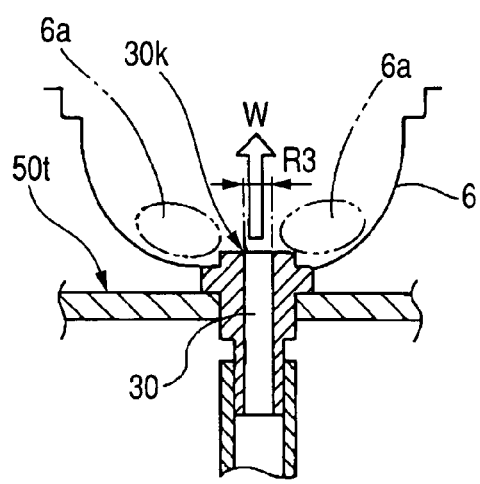
FIG. 11 is a partial cross-sectional view illustrating a conventional liquid-fluid discharge port of a case channel illustrated in FIG. 4 as well as a washing case.
Figure 12:
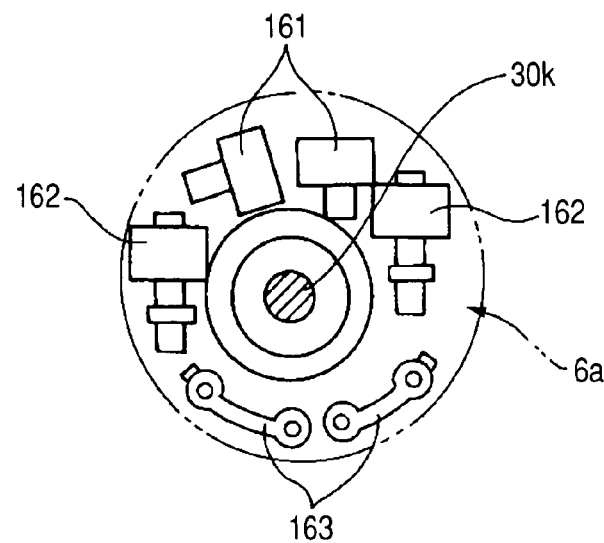
FIG. 12 is a top view illustrating a positional arrangement, in a washing case, of various types of buttons of two endoscopes, when liquid-fluid is discharged from the conventional liquid-fluid discharge port.
Figure 13:
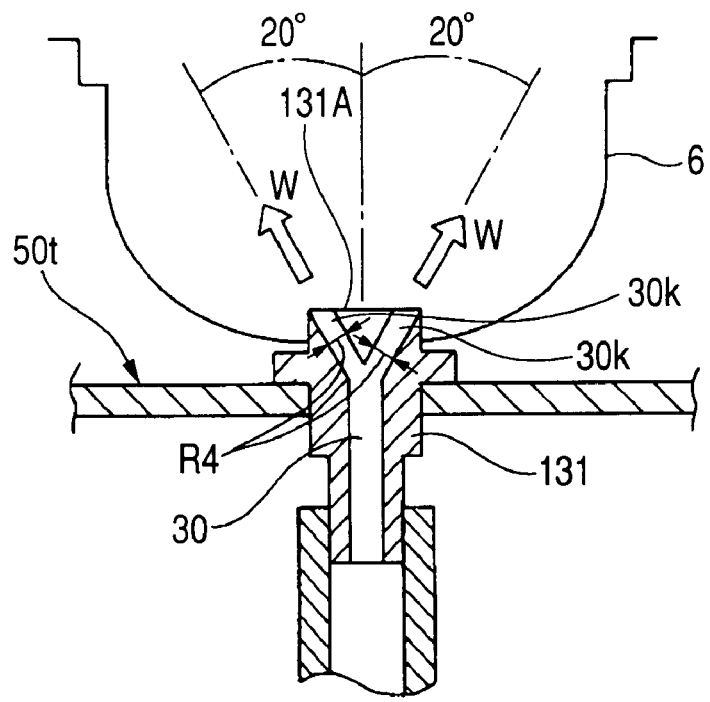
FIG. 13 is a partial cross-sectional view illustrating, together with a washing case, a liquid-fluid discharge port of a case channel in case four liquid-fluid discharge ports are opened, each being inclined by 20° with respect to a vertical direction.
Figure 14:
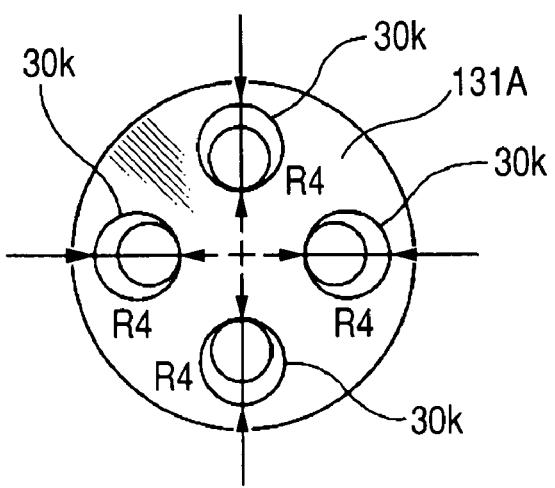
FIG. 14 is a top view of the liquid-fluid discharge port illustrated in FIG. 13.

FIG. 9 is an enlarged perspective view of the washing case illustrated in FIG. 1. FIG. 10 illustrates a state where a cover of the washing case illustrated in FIG. 9 has been opened. FIG. 11 is a partial cross-sectional view illustrating a conventional liquid-fluid discharge port of a case channel illustrated in FIG. 4 as well as a washing case. Furthermore, FIG. 12 is a top view illustrating a positional arrangement, in a washing case, of various types of buttons of two endoscopes, when liquid-fluid is discharged from the conventional liquid-fluid discharge port. FIG. 13 is a partial cross-sectional view illustrating, together with a washing case, a liquid-fluid discharge port of a case channel in case four liquid-fluid discharge ports are opened, each being inclined by 20° with respect to a vertical direction. FIG. 14 is a top view of the liquid-fluid discharge port illustrated in FIG. 13.

When washing/disinfecting the outer surfaces, and the interiors of the AW channels 101, 111, and the S channels 102, 112 of the first and second endoscopes 100 and 110 in the washing/disinfecting vessel 4 of the apparatus body 2 of the washing/disinfecting apparatus 1 as described above, buttons, such as air-water supply buttons (hereinafter referred to as "AW button(s)") 162 such as for each of scope switches, suction buttons (hereinafter referred to as "S button(s)") 161, and forceps (or forcipes) 163 removed from the connector ports 99 or 199 of the S channels 102 or 112, are accommodated, as shown in FIG. 10, in a washing case 6 shown in FIG. 7 by opening/closing a cover 6t so as to be washed/disinfected.

Specifically, liquid-fluid W, such as the washing liquid or the disinfecting liquid, that has been sucked from the circulator port 56 of the washing/disinfecting vessel 4 into the circulation channel 20 and channel 21 with the aid of the channel pump 26, is blown out into the washing case 6, through the channel block 27, from a single liquid-fluid discharge port 30k of a case channel 30 while the CH electromagnetic valve 28 is open. The discharge port 30k has an opening diameter R3=φ5.6 mm, for example, and is opened in the washing case 6. As a result, the AW buttons 162, the S buttons 161 and the forceps 163 immersed in the washing and disinfecting liquids are washed/disinfected. In this case, ultrasonic vibration of the ultrasonic transducers 52 ensures reliable washing of the AW buttons 162, S buttons 161 and forcipes 163.

When the liquid-fluid W is blown out into the washing case 6, the AW buttons 162, S buttons 161 and forcipes 163 accommodated in the washing case 6 are whirled around by the liquid-fluid W. This removes the foam attached to the outer surfaces of the AW buttons 162, S buttons 161 and forcipes 163. Therefore, the AW buttons 162, S buttons 161 and forcipes 163 can be efficiently washed in performing disinfection.

As shown in FIG. 11, the liquid-fluid port 30k is opened with the case channel 30 being extensively lengthened from the bottom face 50t of the vessel body 50 of the washing/disinfecting vessel 4, so that discharge port 30k will be oriented upward in a direction perpendicular to the bottom face 50t. In other words, the discharge port 30k is opened in such a way that the liquid-fluid W can be discharged upward in the vertical direction. This arrangement has raised a problem that, as shown in FIG. 11, stream of the liquid-fluid W is structurally weak in a region 6a around the discharge port 30k In the washing case 6.

When washing/disinfecting the two endoscopes, i.e. the first and second endoscopes 100 and 110, in the endoscope washing/disinfecting apparatus 1 as described above, the number of the AW buttons 162, S buttons 161 and forcipes 163 removed from the endoscopes 100 and 110 is six in total, which is twice as large as that of the case of washing/disinfecting a single endoscope. Thus, the AW buttons 162, S buttons 161 and forcipes 163 totaling six in number have to be accommodated and washed/disinfected in the washing case 6.

Since the number of the AW buttons 162, S buttons 161 and forcipes 163 to be accommodated in the washing case 6 has been increased, the AW buttons 162, S buttons 161 and forcipes 163 totaling six in number are unavoidably densely accommodated in the region 6a of the washing case 6, in which the stream of the liquid-fluid W is weak as mentioned above. As a result, the total of six AW buttons 162, S buttons 161 and forcipes 163 are not whirled, or only whirled weakly. This has raised a problematic difficulty in removing the foam.

Considering such a problem as described above, the opening diameter of the discharge port 30k may be reduced while raising the flow speed of the liquid-fluid W, so that the total of six AW buttons 162, S buttons 161 and forcipes 163 can be forcedly whirled. However, higher flow speed may deteriorate the durability of the six AW buttons 162, S buttons 161 and forcipes 163. Further, use of the channel pump 26 having higher performance than the conventional one, may raise another problem of increasing cost.

Thus, in view of the above problem, it is desirable to maintain the durability of the six AW buttons 162, S buttons 161 and forcipes 163 of the two endoscopes, and at the same time to reliably perform washing/disinfection by causing whirl in the washing case 6 for removal of the foam, without increasing the manufacturing cost of the manufacturing apparatus. To this end, as shown in FIGS. 13 and 14, the case channel 30 is branched to provide four discharge ports 30k with an even interval therebetween. Further, the opening direction of each of the four discharge ports 30k is set so as to be directed upward with an inclination of 10° to 30°, e.g. 20°, with respect to the vertical direction. Also, an opening diameter R4 of each of the four discharge ports 30k is set to be φ2.0 to φ2.1 mm.

In this way, the liquid-fluid W is radially discharged from the four discharge ports 30k to strengthen the stream in the region 6a, whereby the total of six AW buttons 162, S buttons 161 and forcipes 163 can be reliably whirled.

The reason why the discharge ports 30k are inclined by 10° to 30° with respect to the vertical direction is that an angle larger or smaller than the 10° to 30° may weaken the stream in the region 6a, and thus whirling of the six AW buttons 162, S buttons 161 and forcipes 163 is weakened.

Further, the reason why the opening diameter R4 of each discharge port 30k is set at a value selected from a range of φ2.0 to φ2.1 mm is that, the conventional opening diameter R3=φ5.6 mm may weaken the flow speed in case of four discharge ports. Another reason is that the opening diameter less than R4 of φ2.0 mm may provide so excessively a high flow speed in the region 6a that the durability of the AW buttons 162, S buttons 161 and forcipes 163 may be deteriorated. Accordingly, it is only necessary to form the opening diameter R4 at a value selected from a range of φ2.0 to φ2.1 mm. This was confirmed by the present inventors through experiments.

By providing the discharge ports 30k as described above, the durability of the total of six AW buttons 162, S buttons 161 and forcipes 163 of the two endoscopes can be maintained. At the same time, the total of six AW buttons 162, S buttons 161 and forcipes 163 can be whirled in the washing case 6 for removal of the foam and for reliable washing/disinfection, without raising the cost of the washing/disinfecting apparatus 1.

Figure 15:
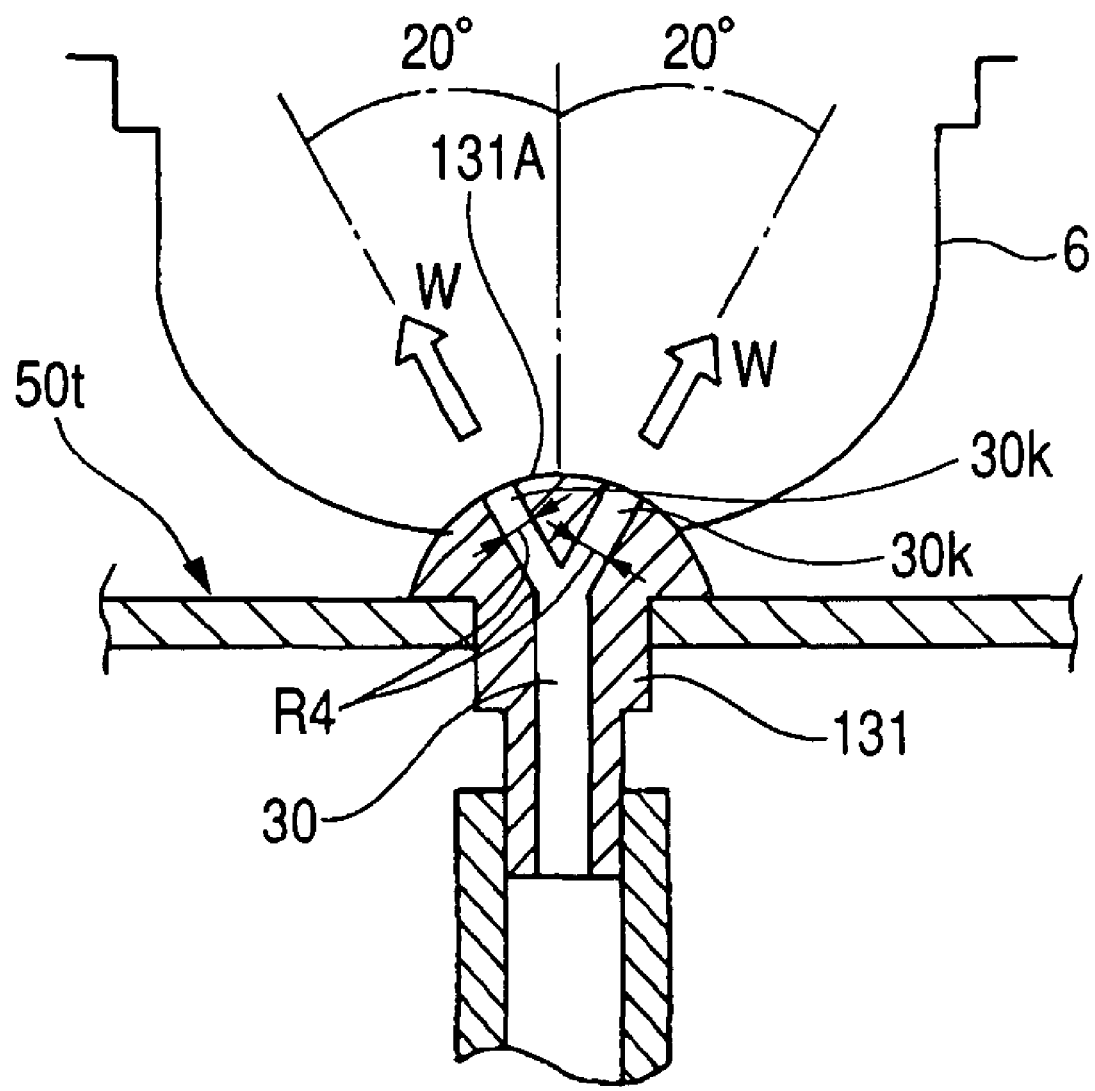
FIG. 15 is a cross-sectional view illustrating another shape of a top end face of a nozzle for providing liquid-fluid discharge ports, according to a second embodiment of the present invention.

In the present invention, an upper end face 131A of a nozzle 131 for providing the four discharge ports 30k has a planar form. Alternatively, however, the end face 131A may be projected to have a hemispherical form, as shown in FIG. 15. This may prevent the inconvenience that would have been caused by erroneously placing the washing case 6 at a position on the upper end face 131A. When the washing case 6 is placed being offset on the end face 131A, a portion of the four discharge ports 30k may be blocked and no proper amount of liquid-fluid may be supplied. Each of the discharge port 30k communicates with a secondary side of a relief valve provided in a channel of the apparatus so as to have a function of depressurizing the channels in the apparatus. If the discharge ports 30k are blocked even partially, the pressure in the channels may be raised to create an erroneous state. However, by providing the hemispherical upper end face 131A as in the modification shown in FIG. 15, the washing case 6 is ensured to have a good seating condition. At the same time, even when the washing case 6 is set being offset, a bottom face of the washing case 6 may slide down on the end face 131A by the deadweight so as to be automatically located at a right position. In this way, a proper amount of liquid-fluid can be constantly obtained, and no erroneous condition may be carelessly brought about.

Third Embodiment

With reference to FIGS. 16 to 20, hereinafter is described an endoscope washing/disinfecting apparatus according to a third embodiment. This embodiment is associated with preventing leakage of liquid to the outside of the apparatus.

Figure 16:
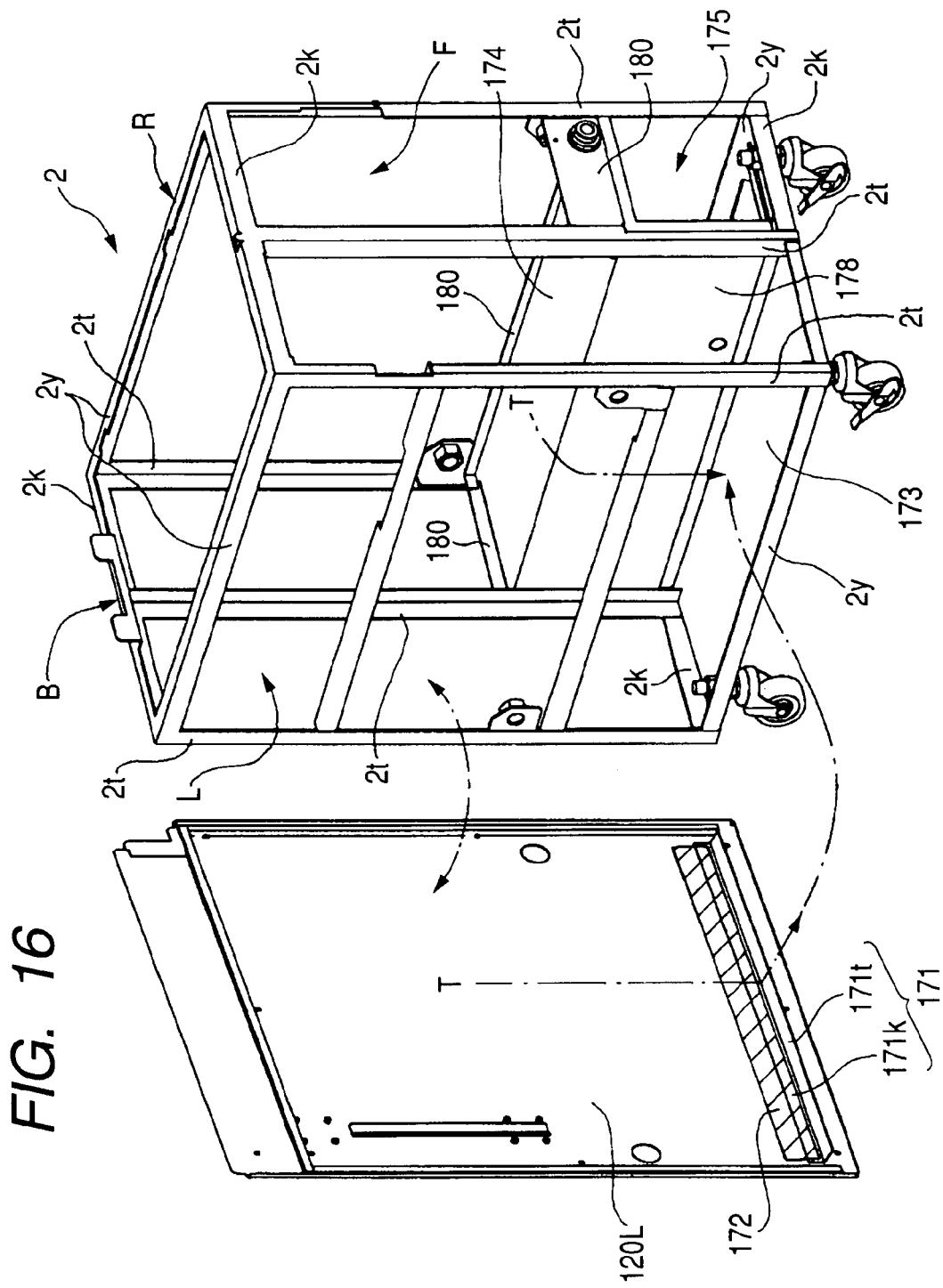
FIG. 16 is a perspective view illustrating an inner structure of the apparatus body illustrated in FIG. 1 with no object being accommodated and with its left-side cover member being detached.
Figure 17:
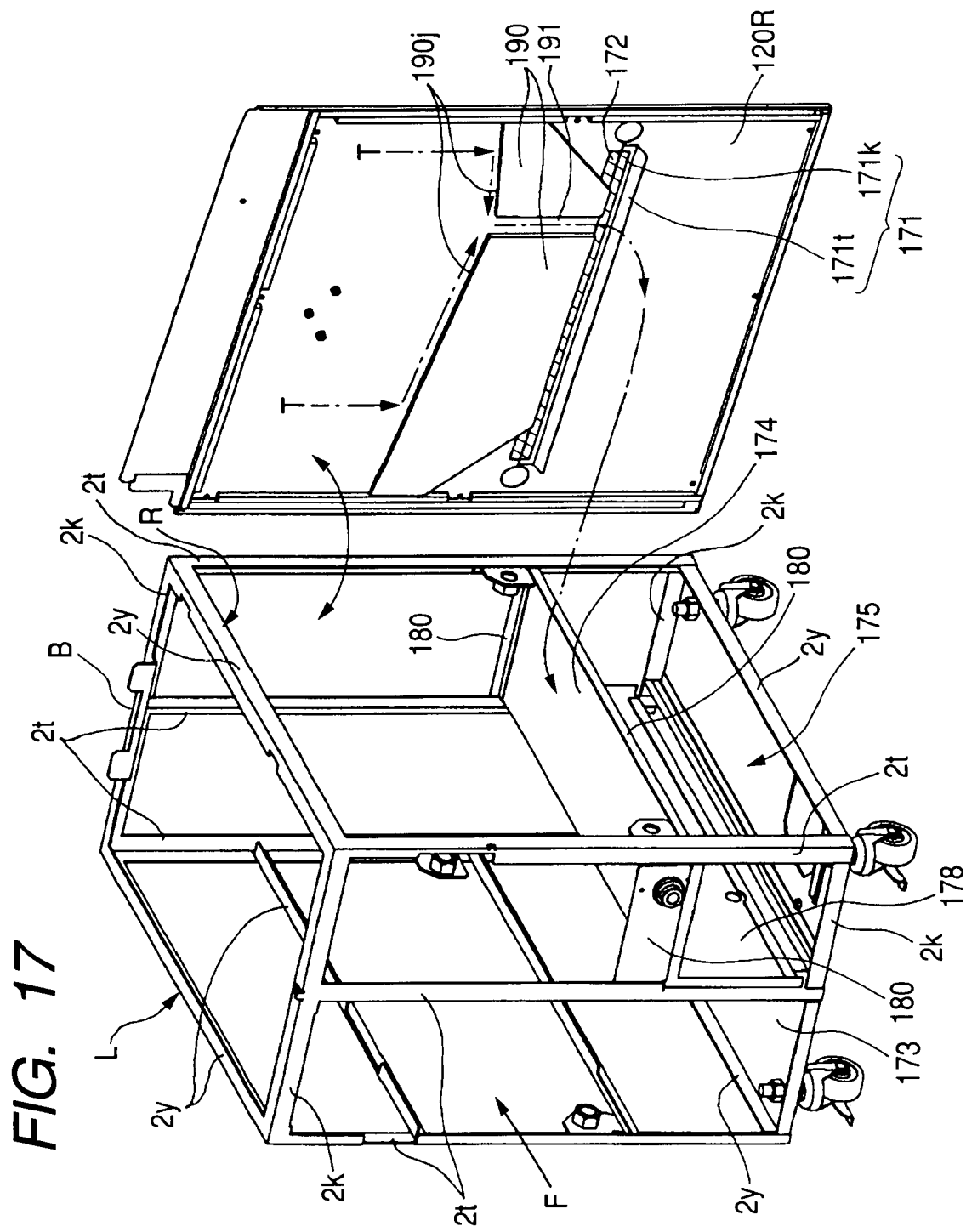
FIG. 17 is a perspective view illustrating an inner structure of the apparatus body illustrated in FIG. 1 with no object being accommodated and with its right-side cover member being detached.

FIG. 16 is a perspective view illustrating an inner structure of the apparatus body illustrated in FIG. 1 with no object being accommodated and with its left-side cover member being detached. FIG. 17 is a perspective view illustrating an inner structure of the apparatus body illustrated in FIG. 1 with no object being accommodated and with its right-side cover member being detached.

Figure 18:
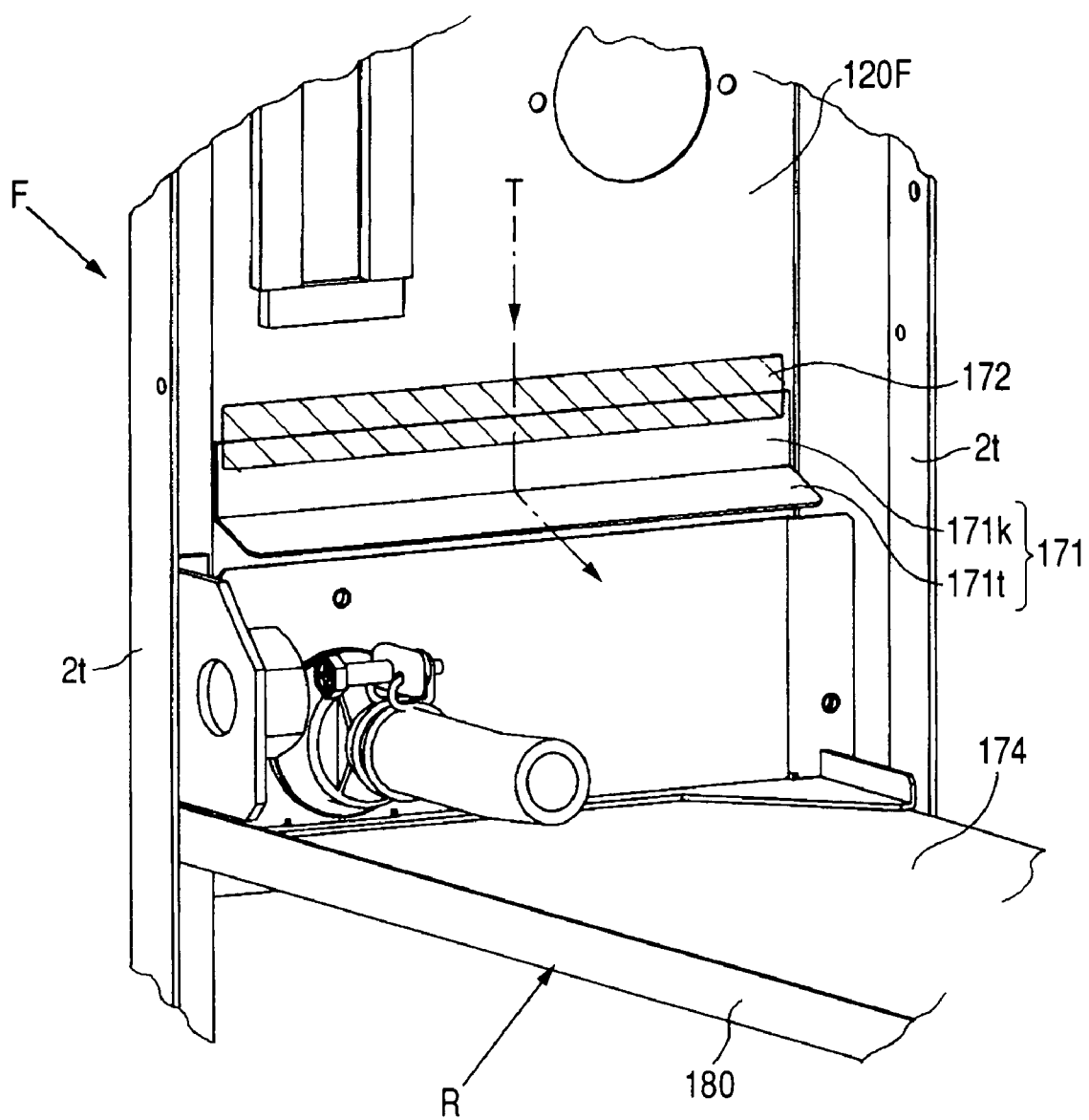
FIG. 18 is a partial perspective view illustrating an inner front structure of the apparatus body illustrated in FIG. 1 with no object being accommodated.
Figure 19:
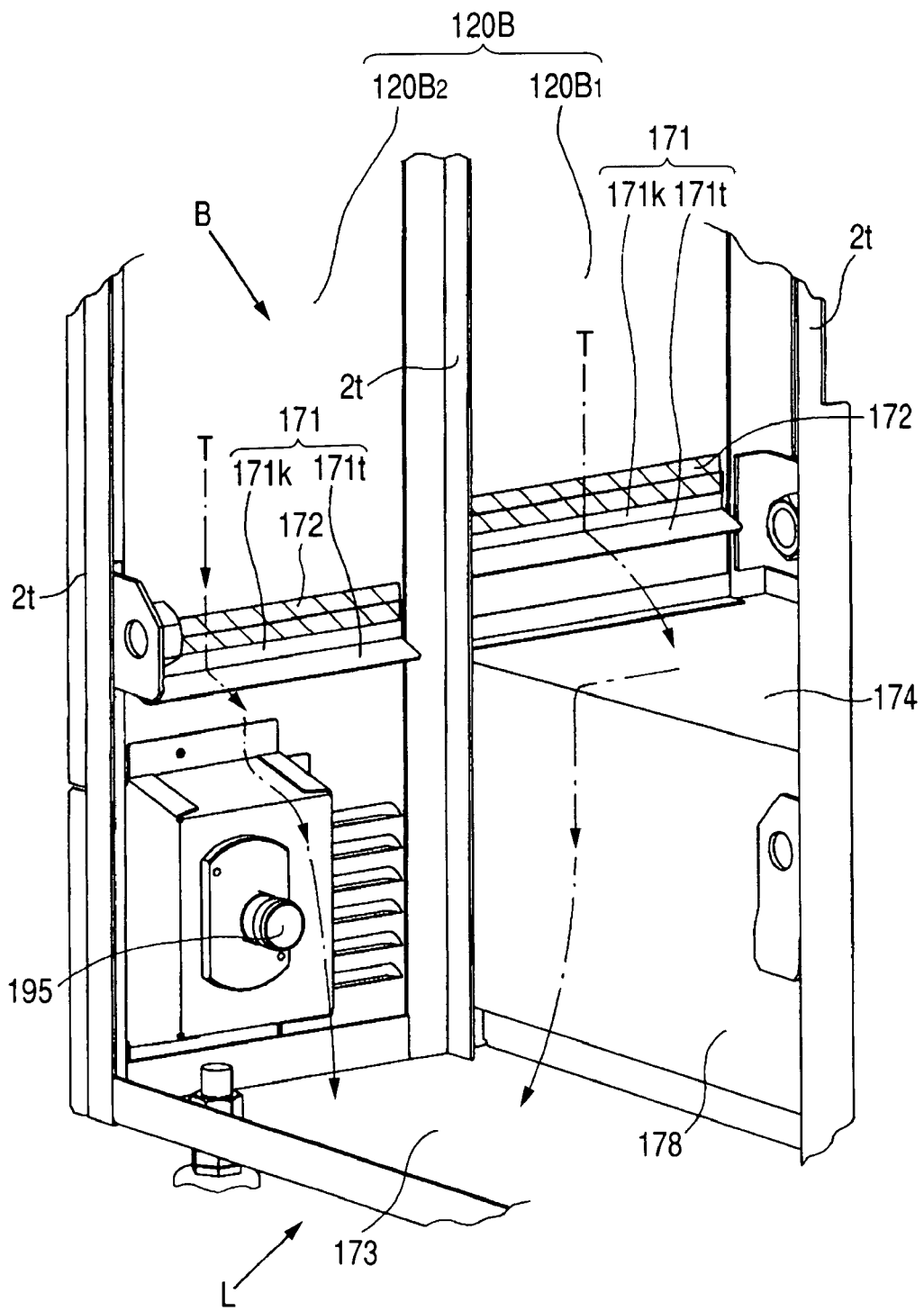
FIG. 19 is a partial perspective view illustrating an inner rear structure of the apparatus body illustrated in FIG. 1 with no object being accommodated.
Figure 20:
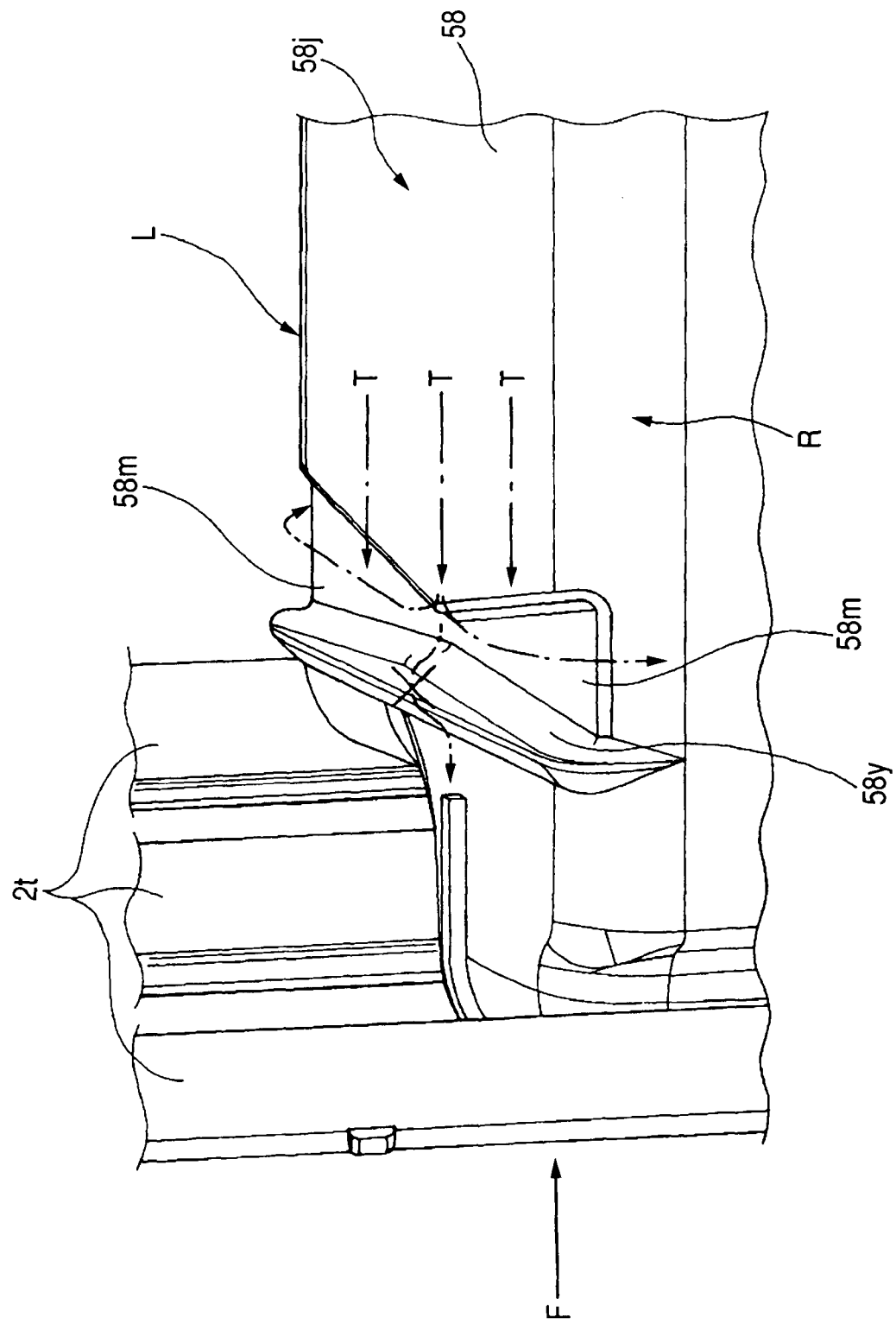
FIG. 20 is a partial perspective view illustrating a top structure of a chemical liquid tank illustrated in FIG. 5, which is mounted on a mounting plate of the apparatus body illustrated in FIG. 16.

Furthermore, FIG. 18 is a partial perspective view illustrating an inner front structure of the apparatus body illustrated in FIG. 1 with no object being accommodated. FIG. 19 is a partial perspective view illustrating an inner rear structure of the apparatus body illustrated in FIG. 1 with no object being accommodated. FIG. 20 is a partial perspective view illustrating a top structure of a chemical liquid tank illustrated in FIG. 5, which is mounted on a mounting plate of the apparatus body illustrated in FIG. 16.

In the endoscope washing/disinfecting apparatus according to the present embodiment, a front face F, a rear face B, a right face R and a left face L to which an operator approaches, are covered with plate-like cover members 120F, 120B, 120R and 120L, respectively. Hereinafter, the side of the cover member 120F is referred to as "front", the side of the cover member 120B as "rear", the side of the cover member 120R as "right" and the side of the cover member 120L as "left".

Specifically, as shown in FIGS. 16 to 19, framing of the apparatus body 2 is made up of a plurality of longitudinal posts 2y extending in a direction for linking between the front face F and the rear face B at a top and a bottom of the apparatus body 2, a plurality of lateral posts 2k extending in a direction for linking between the right face R and the left face L at the top and the bottom of the apparatus body 2, and a plurality of vertical posts 2t extending in a direction for linking between the top and the bottom of the apparatus body 2.

The front cover member 120F can be freely fixed to the two upper and lower lateral posts 2k and the three vertical posts 2t on the front face F, and the rear cover member 120B can be freely fixed to the two upper and lower lateral posts 2k and the three vertical posts 2t on the rear face B.

The right cover member 120R can be freely fixed to the two upper and lower longitudinal posts 2y and the two vertical posts 2t on the right face R, and the left cover member 120L can be freely fixed to the two upper and lower longitudinal posts 2y and the two vertical posts 2t on the left face L.

In the apparatus body 2 covered with the four cover members 120F, 120B, 120R and 120L, the plurality of channels for flowing the washing liquid and the disinfecting liquid are accommodated as have been shown in FIG. 4.

Assuming that the plurality of channels are broken for some reasons to cause leakage therefrom, the leaked washing liquid, the disinfecting liquid or the like (hereinafter referred to as "leak liquid T") is generally adapted to be collected to a bottom face, or a drain pan 173, which is fixed, as shown in FIG. 16, to the two lower longitudinal posts 2y and the two lateral posts 2k of the apparatus body 2.

When the leak liquid T collected to the drain pan 173 has reached a certain level or exceeded the certain level, a leak detector turns on to produce a detection signal. Receiving the detection signal, the control unit 70 (see FIG. 4) controls the feed-water electromagnetic valve 15 (see FIG. 4) so that no more leak occurs in the apparatus body 2.

It is so arranged that a warning, for example, is then indicated on the sub-operation panel 13 (see FIG. 1) by the control unit 70, so that a service person, for example, called for by a user can take off a stopper, not shown, in the drain pan 173 to remove the leak liquid T from the drain pan 173.

However, in case leakage has occurred at a plurality of channels, the leak liquid T may not necessarily be entirely collected to the drain pan 173. Specifically, the leak liquid T that has attached to the inner face of the cover member 120L, for example, and runs down along the inner face of the cover member 120L may leak out of the apparatus body 2 from between a lower part of the inner face of the cover member 120L and the longitudinal post 2y on the left face L. Possibly, the leak liquid T may not be collected to the drain pan 173 but may scatter to and remain at various portions of the apparatus body 2 other than the drain pan 173.

In such cases, a problem may arise that the leak sensor mentioned above cannot correctly detect the amount of the leak liquid T, and that failure may be caused in electrical components accommodated in the apparatus body 2 by the scattered leak liquid T.

In addition, in case the un-diluted disinfecting liquid contained in the chemical liquid bottle 12a, is leaked at the time of accommodating the bottle 12a in the cassette tray 12, the high concentration disinfecting liquid may remain in the apparatus body 2, or may be leaked out of the apparatus body 2.

Thus, an arrangement has been desired in which the leak liquid T will not leaked out of the apparatus body 2 and will be reliably directed only to the drain pan 173 even when the leak liquid T has leaked out of a plurality of channels in the apparatus body 2.

In light of the circumstances described above, in the apparatus body 2 of the washing/disinfecting apparatus 1 according to the present embodiment, an L-shaped projecting plate 171 is provided extending widthwise on an inner face of the cover member 120L, as shown in FIG. 13. The projecting plate 171 is provided so as to be located closely above the drain pan 173 when the cover member 120L is fixed onto the left face L. The projecting plate 171 is provided with a projecting portion 171t which is slanted downward by about 20° with respect to a direction perpendicular to the inner face of the cover member 120L and projected by 20 mm, for example, toward the drain pan 173.

The projecting plate 171 has a shape of a rail extending widthwise on the inner face of the cover member 120R, with the fixing portion 171k being fixed to the inner face of the cover member 120L.

With this arrangement, the leak liquid T that has scattered from a plurality of channels and has attached to the inner face of the cover member 120L runs down along the inner face of the cover member 120L, as shown in FIG. 16, and then is reliably directed to the drain pan 173 by the projecting portion 171t of the projecting plate 171.

In this case, since a seal member 172 is applied to fill a gap made between an upper side of a fixing portion 171k of the projecting plate 171 and the inner face of the cover member 120L, the leak liquid T that has run down along the cover member 120L may not pass through this gap. In other words, the leak liquid T may not leak out of the apparatus body 2 from between the inner face of the cover member 120L and the longitudinal post 2y.

As shown in FIG. 17, an electric components storage portion 175 is provided in the apparatus body 2. The storage portion 175 is located at a lower part of the right face R, extending widthwise on the right face R.

A mounting plate 174 which covers a top of the storage portion 175 and on which the chemical liquid tank 58 described above is placed is provided above the storage portion 175. The mounting plate 174 is fixed to the vertical posts 2t on the front face F and the rear face B so as to be parallel to the drain pan 173. The mounting plate 174 is fixed at a predetermined level from the drain pan 173.

As shown in FIGS. 16 and 17, a left side face of the storage portion 175 is covered with a longitudinal plate 178 which is perpendicular to the drain pan 173. The longitudinal plate 178 links a right side end of the drain pan 173 to a left side end of the mounting plate 174 and extends along a direction connecting the front face F and the rear face B. The mounting plate 174 and the longitudinal plate 178 prevent the leak liquid T from attaching, from inside the apparatus body 2, to the electric components stored in the storage portion 175.

As shown in FIG. 20, the chemical liquid tank 58 placed on the mounting plate 174 is formed, on its upper face 58j, with a ridge 58y of a predetermined height. The ridge 58y is located frontward of the apparatus body 2 and extends widthwise, i.e. along a direction connecting the right side and the left side of the tank 58. Further, a groove 58m is formed in the upper face 58j of the chemical liquid tank 58. The groove 58m Is located closely behind the ridge 58y and extends widthwise of the tank 58.

Thus, even when the leak liquid T attaches to the upper face 58j of the tank 58, the leak liquid T can be directed only to the cover member 120R or the drain pan 173. Since the leak liquid T cannot climb over the ridge 58y, the leak liquid T on the upper face 58j will not run down from the front of the tank 58.

When the chemical liquid bottle 12a has been set in the cassette tray 12, the ridge 58y and the groove 58m are located between an injection port 12ak (see FIG. 25 described later) of the bottle 12a and the vertical posts 2t on the front face F. Therefore, a stock solution of the disinfecting liquid that has fallen on the upper face 58j can be reliably directed to the cover member 120R or the drain pan 173 with the aid of the ridge 58y and the groove 58m.

Further, a spongy heat insulator 190 is provided on the inner face of the cover member 120R, so as to be in contact with a face of the tank 58 on the side of the cover member 120R when the tank is placed on the mounting plate 174.

The heat insulator 190 plays a roll of preventing temperature of the disinfecting liquid in the tank 58 from lowering. The heat insulator 190 is fixed onto the inner face of the cover member 120R in such a way that an upper side 190j of the heat insulator 190 is positioned lower than the upper face 58j of the tank 58 when the heat insulator 190 is brought into contact with the tank 58.

As shown in FIG. 17, the heat insulator 190 is divided into two, separated in an anteroposterior direction and fixed. The upper side 190j of each of the pieces of the heat insulator 190 is slanted toward a region 191 which is formed between the two pieces of the heat insulator 190. The two pieces of heat insulator 190 is fixed onto the inner face of the cover member 120R extending widthwise on the inner face of the cover member 120R.

Thus, the leak liquid T that has been directed from the upper face 58j of the chemical liquid tank 58 placed on the mounting plate 174, onto the inner face of the cover member 120R with the aid of the ridge 58y and the groove 58m can be reliably directed to the region 191 making use of the inclination of the upper side 190j of the two pieces of heat insulator 190. Similarly, the leak liquid T that has attached to the inner face of the cover member 120R above the heat insulator 190 and then has run down along the inner face of the cover member 120R, can be reliably directed to the region 191 making use of the inclination of the upper side 190j of the two pieces of heat insulator 190.

Since the two pieces of heat insulator 190 are each in contact with the vertical posts 2t on the side of the front face F, even when the leak liquid T has attached to these vertical posts 2t, the leak liquid T can be reliably directed to the region 191 by the upper side 190j of the two pieces of heat insulator 190.

As shown in FIG. 17, the L-shaped projecting plate 171 mentioned above is provided widthwise on the inner face of the cover member 120R. The projecting plate 171 is provided so as to be located closely above the mounting plate 174 when the cover member 120R is fixed onto the right face R. The projecting plate 171 is provided with a projecting portion 171t which is slanted downward by about 20° with respect to a direction perpendicular to the inner face of the cover member 120R and projected by 20 mm, for example, toward the mounting plate 174.

The projecting plate 171 has a shape of a rail extending widthwise on the inner face of the cover member 120R, with the fixing portion 171k being fixed to the inner face of the cover member 120R.

Thus, as shown in FIG. 17, the leak liquid T that has fallen down from the region 191 between the two pieces of heat insulator 190 can be reliably directed to the mounting plate 174 by the projecting portion 171t of the projecting plate 171.

In this case as well, the seal member 172 is applied to a gap made between the upper side of the projecting portion 171k of the projecting plate 171 and the inner face of the cover member 120R so that the gap can be filled. Therefore, the leak liquid T does not pass through the gap. In other words, the leak liquid T does not leak out of the apparatus body 2 from between the cover member 120R and the longitudinal post 2y.

The leak liquid T that has been directed to the mounting plate 174 is adapted to fall onto the drain pan 173 along the longitudinal plate 178. A wall plate 180 having a predetermined height is provided to the mounting plate 174 along a side on the side of the front face F, along a side on the side of the right face R and along a side on the side of the rear face B.

Thus, the leak liquid T that has fallen on the mounting plate 174 does not further fall down from the side of the front face F, the right face R and the rear face B of the mounting plate 174 owing to the wall plates 180. In other words, the leak liquid T can be reliably directed to the drain pan 173 running down on the longitudinal plate 178.

As shown in FIG. 18, the L-shaped projecting plate 171 is provided extending on an inner face of the cover member 120F of the front face F. The projecting plate 171 is provided so as to be located closely above the mounting plate 174 when the cover member 120F is fixed onto the front face F. The projecting plate 171 is provided with a projecting portion 171*t* which is slanted downward by about 20° with respect to a direction perpendicular to the inner face of the cover member 120F and projected by 20 mm, for example, toward the mounting plate 174.

In this case as well, the projecting plate 171 has a shape of a rail extending widthwise on the inner face of the cover member 120F, with the fixing portion 171*k* being fixed to the inner face of the cover member 120F.

Thus, as shown in FIG. 18, the leak liquid T that has attached to the inner face of the cover member 120F and has fallen down can be reliably directed to the mounting plate 174 by the projecting portion 171*t* of the projecting plate 171.

Also, since the seal member 172 is applied to a gap made between the upper side of the fixing portion 171*k* of the projecting plate 171 and the inner face of the cover member 120F, the leak liquid T does not pass through the gap.

As shown in FIG. 19, the cover member 120B of the rear face B is made up of a cover member 120B1 which is fixed to the vertical post 2*t* in the middle of the rear face B and the vertical post 2*t* on the side of the right face R, and a cover member 120B2 which is fixed to the vertical post 2*t* in the middle of the rear face B and the vertical post 2*t* on the side of the left face L.

The L-shaped projecting plate 171 mentioned above is provided extending widthwise on an inner face of the cover member 120B1. The projecting plate 171 is provided so as to be located closely above the mounting plate 174 when the cover member 120B is fixed to the rear face B. The projecting plate 171 is provided with a projecting portion 171*t* which is slanted downward by about 20° with respect to a direction perpendicular to the inner face of the cover member 120B and projected by 20 mm, for example, toward the mounting plate 174.

The projecting plate 171 has a shape of a rail extending widthwise on the inner face of the cover member 120B1 with the fixing portion 171*k* being fixed to the inner face of the cover member 120B1.

Thus, as shown in FIG. 19, the leak liquid T attached to the inner face of the cover member 120B1 can be reliably directed to the mounting plate 174 by the projecting portion 171*t* of the projecting plate 171, and then is directed to the drain pan 173 running down on the longitudinal plate 178 as described above.

Also, the seal member 172 is applied to a gap made between the upper side of the projecting portion 171*k* of the projecting plate 171 and the inner face of the cover member 120B1 in order to fill the gap. Therefore, the leak liquid T does not pass through the gap.

The L-shaped projecting plate 171 is provided extending widthwise on an inner face of the cover member 120B2. The projecting plate 171 is provided so as to be located closely above a metal plate of a portion 195 to which the discharge channel 59 explained above referring to FIG. 4 is connected. The projecting plate 171 is provided with a projecting portion 171*t* which is slanted downward by about 20° with respect to a direction perpendicular to the inner face of the cover member 120B2 and projected by 20 mm, for example, toward the drain pan 173.

The projecting plate 171 has a shape of a rail extending widthwise on the inner face of the cover member 120B2 with the fixing portion 171*k* being fixed to the inner face of the cover member 120B2.

Thus, the leak liquid T that has attached to the inner face of the cover member 120B and has fallen down can be reliably directed to the drain pan 173 by the projecting portion 171*t* of the projecting plate 171, as shown in FIG. 19.

In this case as well, the seal member 172 is applied to a gap made between the upper side of the fixing portion 171*k* of the projecting plate 171 and the inner face of the cover member 120B2 so as to fill the gap. Therefore, the leak liquid T does not pass through the gap.

It will be appreciated that the plurality of channels that may cause leak are not placed below the projecting plates 171 which are fixed to the respective inner faces of the cover members 120L, 120R, 120F and 120B. Accordingly, there is no problem if the leak liquid T has attached to the regions of the cover members 120L, 120R, 120F and 120B below the respective projecting plates 171. Thus, the leak liquid T can be reliably prevented from attaching to the electric components.

As described above, arrangements are schemed in the apparatus body 2 in order to direct the leak liquid T to the drain pan 173. Therefore, leak of the leak liquid T to the outside of the apparatus body 2 can be significantly reduced, and thus user's safety is enhanced. At the same time, the leak liquid T scattered in the apparatus body 2 can be reliably prevented from attaching to the electrical components and thus from causing failure to the electric components.

The reliable direction of the leak liquid T to the drain pan 173 may enable the leak sensor provided in the drain pan 173 or close to the drain pan 173 to perform correct detection of the amount of the leak liquid T.

Fourth Embodiment

With reference to FIGS. 21 to 25, hereinafter will be described an endoscope washing/disinfecting apparatus 1 according to a fourth embodiment of the present invention. The present embodiment is associated with facilitated confirmation of a level of chemical liquid contained in the chemical liquid bottles in the apparatus.

In the present embodiment, with the setting of the chemical liquid bottles 12*a*, 12*b* In the cassette tray 12, the injection ports 12*ak*, 12*bk* (see FIG. 25) of the bottles 12*a*, 12*b*, respectively, are inserted into a cassette insertion hole 220 (described later (see FIG. 23)) which is provided in the apparatus body 2. Thus, the disinfectant in the bottle 12*a* and the buffer agent in the bottle 12*b* pass through the chemical liquid supply channel 62 (see FIG. 4) and are supplied to the chemical liquid tank 58.

The bottles 12*a*, 12*b* are often so arranged that they are set at the cassette tray 12 being slanted downward in order to improve the efficiency of injecting chemical liquid. Therefore, when the injection ports 12*ak*, 12*bk* of the bottles 12*a*, 12*b*, respectively, are detached from the cassette insertion hole 220, some droplets of the disinfectant and the buffer agent may run from the bottles and enter the interior of the apparatus body 2. Hereinafter, the leaked disinfectant and buffer agent are referred to as "leak liquid T".

In order to prevent scattering of the leak liquid T leaked out of the injection ports 12*ak*, 12*bk* in the apparatus body 2, a drip pan may generally be provided closely below the injection ports 12*ak*, 12*bk* of the bottles 12*a*, 12*b*.

However, when the insertion of the injection ports 12*ak*, 12*bk* of the bottles 12*a*, 12*b* into the cassette insertion hole 220 is incomplete, and this incomplete state is kept for a long time, a large volume of leak liquid T may be leaked from the injection ports 12ak, 12bk.

As described above, leak can be detected by the leak detector in the drain pan 173. However, if the leak sensor is set to react only when about one liter, for example, of the leak liquid T has been collected to the drain pan 173, collection of, say, only ⅓ litter of the leak liquid T in the drain pan 173 would not be detected by the leak sensor. As a result, a user may not be informed of the leak from the bottles 12a, 12b in such a case, and this has been a problem. Therefore, an arrangement has been desired in which leak from the bottles 12a, 12b can be reliably detected.

Under the circumstances described above, the apparatus body 2 of the endoscope washing/disinfecting apparatus 1 according to the present embodiment employs an arrangement in which a stock solution leak sensor 205, such as an electrode sensor, is provided in a drip pan 200 which is provided closely below the injection ports 12ak, 12bk of the bottles 12a, 12b.

Figure 21:
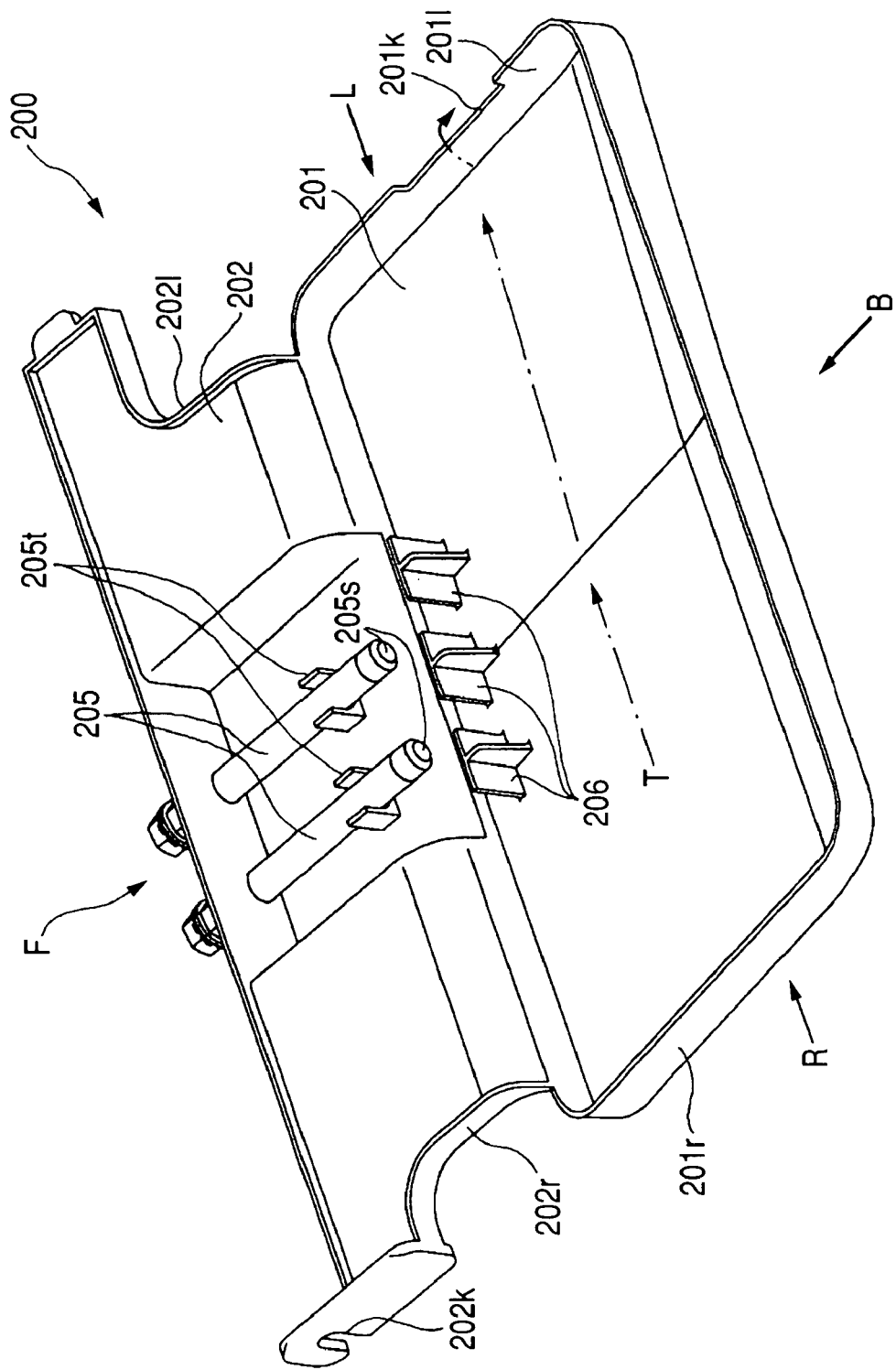
FIG. 21 is a perspective view of a drip pan arranged below the injection ports of the chemical liquid bottles in the apparatus body illustrated in FIG. 1.

Specifically, as shown in FIG. 21, the drip pan 200 is made up of a tray member 201 and an attaching member 202. By fixing a fixing portion 202k of the attaching member 202 to the apparatus body 2 using a screw, for example, the drip pan 200 is disposed above the chemical liquid tank 58 and closely below the injection ports 12ak, 12bk of the bottles 12a, 12b. As shown in FIG. 21, the drip pan 200 is fixed in such a way that a right side end 201r Is located close to the cover member 120R of the apparatus body 2, and that a left side end 201l is located close to the drain pan 173.

Since the drip pan 200 is fixed to the apparatus body 2 through a single screw, the drip pan 200 can be readily detached from the apparatus body 2, and thus can be readily cleaned.

The tray member 201 plays a roll of stocking the leak liquid T leaked from the injection ports 12ak, 12bk of the bottles 12a, 12b. As shown in FIG. 21, a notch 201k is formed at the left side end 201l of the tray member 201. When a large volume of leak liquid T has been stocked in the tray member 201, the notch 201k allows the leak liquid T to overflow therefrom on a priority basis and leads, without fail, the overflowed leak liquid T to the drain pan 173 located at the left side end 201l.

Figure 22:
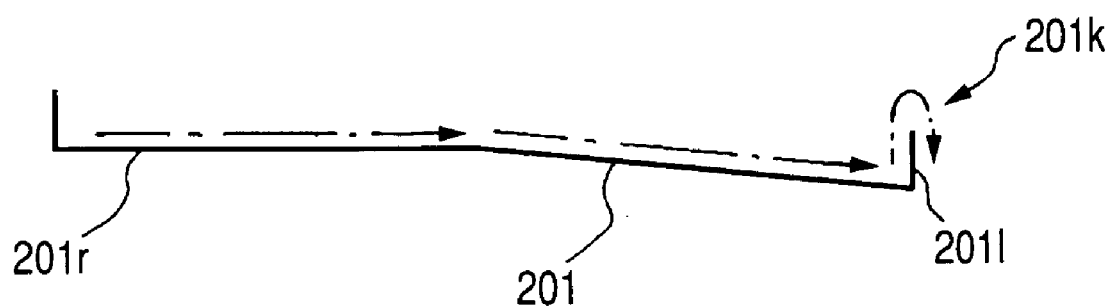
FIG. 22 is a schematic view illustrating inclination of a tray of the drip pan illustrated in FIG. 21.

As shown in FIGS. 21 and 22, a bottom face of a left half of the tray member 201 is adapted to slant downward to the left side end 201l. Thus, the leak liquid T that has fallen onto the tray member 201 is stocked in the left half of the tray member 201 by priority. Accordingly, even when the apparatus body 2 per se has been inclined, the leak liquid T is permitted to overflow from the notch 201k on a priority basis.

The tray member 201 is also provided, on the side of the attaching member 202, with contact prevention members 206 by three in number, for example, being uprising from the bottom face. The contact prevention members 206 play a roll of preventing a user from being in contact with the leak liquid T stocked in the tray member 201, from the side of the front face F of the apparatus body 2.

At substantially the middle of a surface defined by a right side end 202r and a left side end 202l of the attaching member 202, a recess is formed so as to provide a region one step lower than other region. A bottom face of the recess is formed with an inclination of 10°, for example, toward the tray member 201.

Two U-shaped members 205t are provided being fixed to the bottom face of the recess in the attaching member 202. Two stock solution leak sensors 205, for example, are fixedly fitted to the respective two U-shaped members 205t being separated from the bottom face of the recess.

The reason why the two stock solution leak sensors 205 are separated from the bottom face of the recess is to prevent possible erroneous detection of foreign particles or the like by the stock solution leak detectors 205 in case such foreign particles or the like have attached to the bottom face of the recess.

The reason why the two sensors 205 are fixed to the U-shaped members 205t is to prevent contact between the sensors 205, being caused by positional offset or deformation of the sensors 205.

The sensors 205 are fixed to the respective U-shaped members 205t with their tips 205s being positioned lower than the lowest portion of the notch 201k of the tray member 201, so that the sensors 205 can detect the leak liquid T stocked in the tray member 201 before being flowed out of the tray member 201.

With the above arrangement of the drip pan 200 in which the stock solution leak sensors 205 are provided, the leak liquid T, which is so small in amount as cannot be detected by the leak sensor in the drain pan 173, leaked from the injection ports 12ak, 12bk of the chemical liquid bottles 12a, 12b, can be reliably detected.

In this way, a user can be informed of the occurrence of leak in the apparatus body 2 caused at the time of diluting the stock solution of the disinfectant, which may lead to failure in the components around the cassette insertion hole 220 at an earlier stage. Further, since the leak liquid T stocked in the tray member 201 of the dip pan 200 is allowed to overflow from the notch 201k on a priority basis, the leak liquid T can be reliably directed to the drain pan 173. Accordingly, the possible leak of the leak liquid T to the outside of the apparatus body 2 may be reduced, whereby users' safety can be improved.

Figure 23:
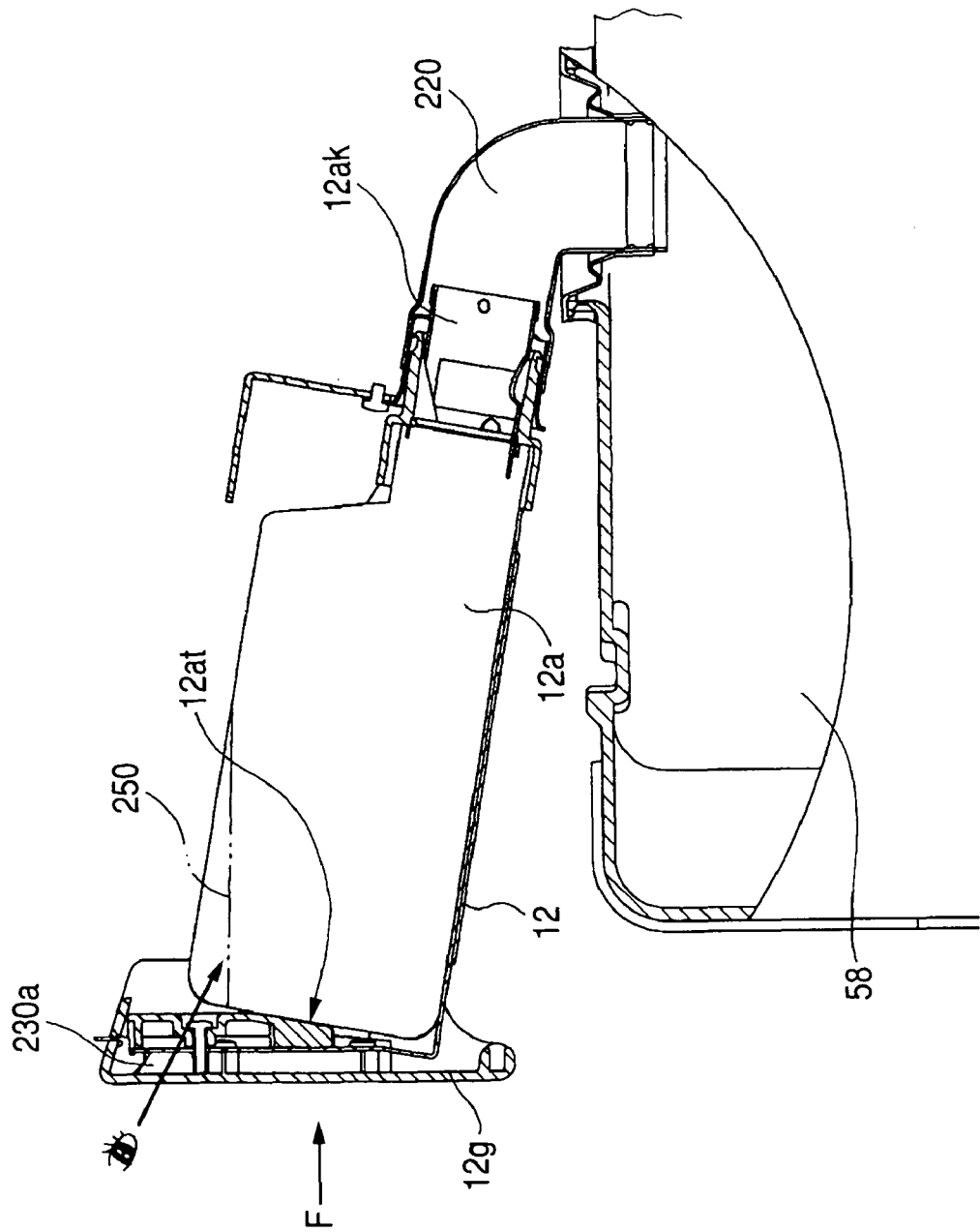
FIG. 23 is an enlarged cross-sectional view illustrating a state where a chemical liquid bottle has been set in a cassette tray illustrated in FIG. 1, together with a cassette insertion hole and the chemical liquid tank.
Figure 24:
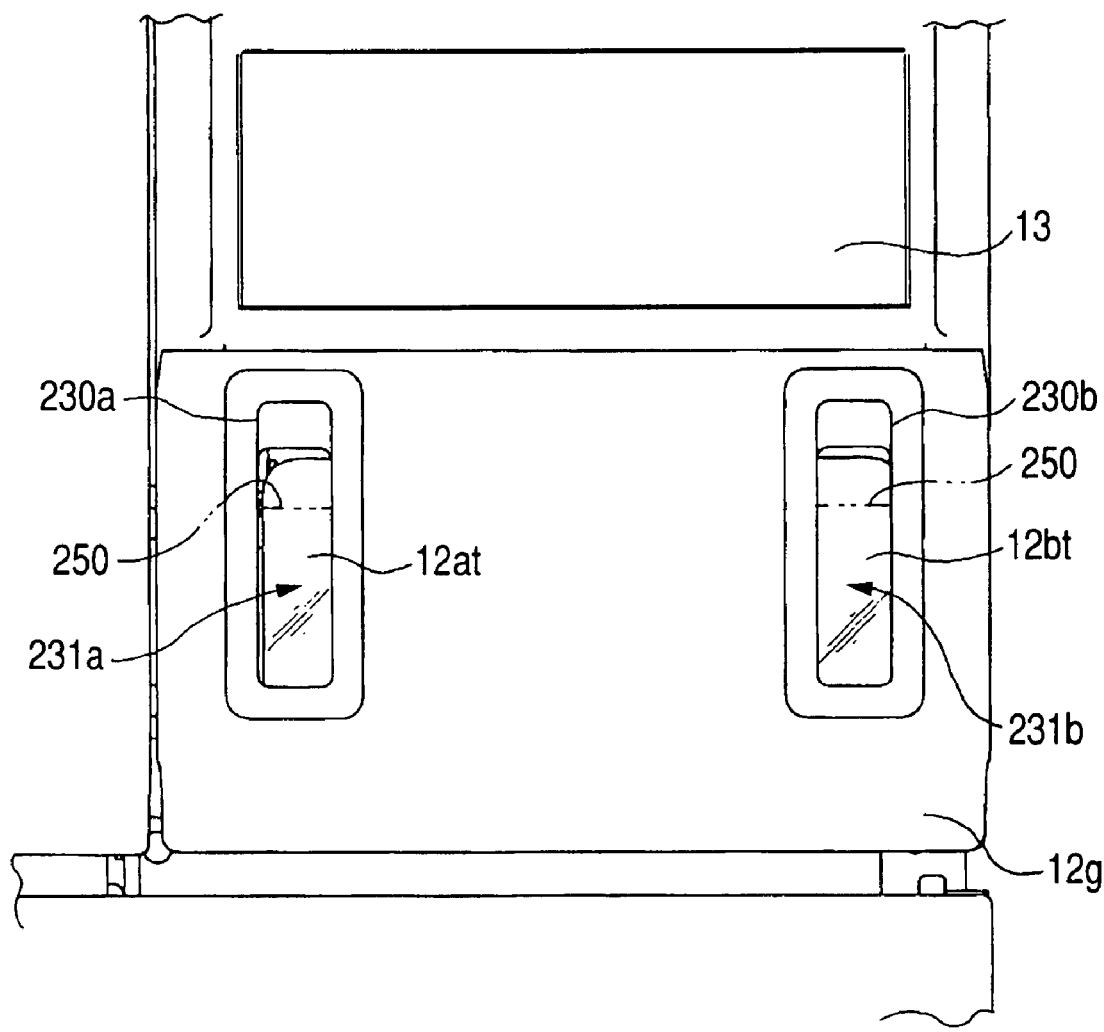
FIG. 24 is a partial enlarged view illustrating an appearance of the apparatus body with observation windows being provided in the cassette tray illustrated in FIG. 1.
Figure 25:
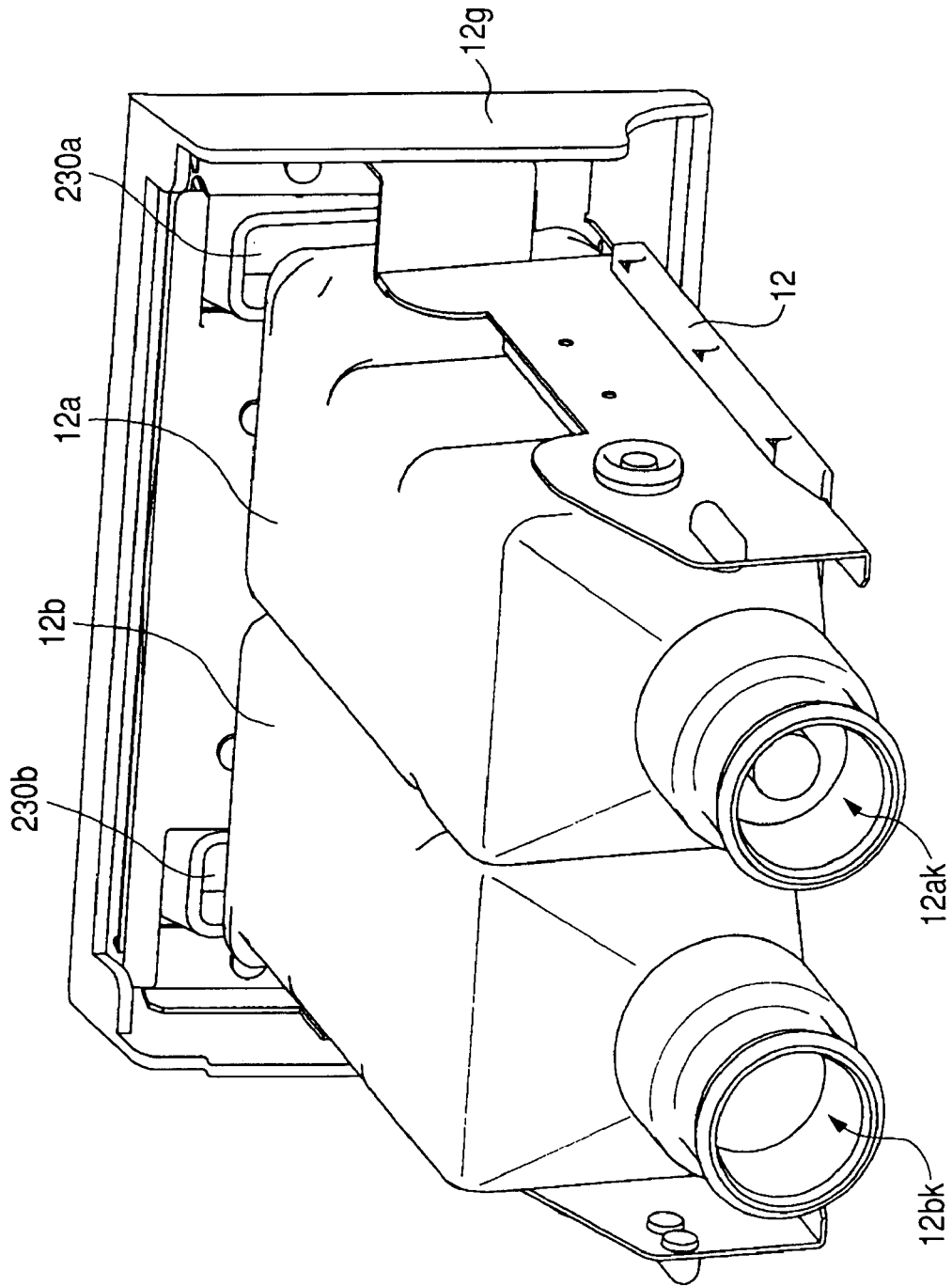
FIG. 25 is an enlarged perspective view illustrating a state where two chemical liquid bottles have been set in the cassette tray illustrated in FIG. 24, as viewed from the inside of the cassette tray.

FIG. 23 is an enlarged cross-sectional view illustrating, together with the cassette insertion hole and the chemical liquid tank, a state where the chemical liquid bottles have been set at the cassette tray illustrated in FIG. 1. FIG. 24 is a partial enlarged view of an appearance of the apparatus body with its cassette tray being provided with observation windows. FIG. 25 is an enlarged perspective view illustrating a state, as viewed from inside, where the two chemical liquid bottles have been set in the cassette tray.

In the apparatus body 2 of the present embodiment, the chemical liquid bottles 12a, 12b are set at the cassette tray 12 being slanted downward as described above. In this case, the apparatus body 2 is so arranged that a sensor, not shown, detects the setting of the bottles 12a, 12b to emit a sound, for example. Thus, a user can be informed of the fact that the bottles 12a, 12b have been correctly set.

However, it has been a problem that the user may not hear the sound due to the surrounding noise, for example. Further, the emission of the sound has nothing to do with the correct injection of the liquids in the bottles 12a, 12b to the chemical liquid tank 58. Thus, it has also been a problem that the user cannot be assured of the fact that the liquids in the bottles 12a, 12b are being injected to the tank 58.

As shown in FIGS. 23 to 25, in the apparatus body 2 according to the present embodiment, observation windows 230a, 230b are formed in a cover member 12g of the cassette tray 12 on the side of the front face F. Through these windows 230a, 230b, a use can observe a level 250 of the liquids, after setting of the cassette tray 12, from the side of a bottom face 12at of the bottle 12a and a bottom face 12bt of the bottle 12b, respectively.

The observation windows 230a, 230b are provided so as to correspond to projections 12am, 12bm (described later (see FIG. 23)), respectively, which form thin portions of the bottom faces 12at, 12bt of the bottles 12a, 12b, respectively. The windows 230a, 230b each have a shape of a so-called oriel window and are slanted downward to the side of the bottom faces 12at, 12bt. That is to say, these windows 230a, 230b are so arranged that the angle of their inclination can each be changed according to the inclination of the bottles 12a, 12b, whereby the use can readily observe the bottom faces 12at, 12bt.

As shown in FIG. 24, the observation windows 230a, 230b each have a vertically elongated form. Owing to this form, a user can observe the bottom faces 12at, 12bt standing, and can confirm, over a longer period of time, the fact of the liquids in the bottles 12a, 12b being injected to the tank 58. Further, the user can attain improved observation properties because the shape of each window ensures a large area on which light is incident.

The bottles 12a, 12b are provided with no air vent port. Therefore, when the chemical liquids are injected to the tank 58, the level 250 of the liquid in each of the bottles 12a, 12b is waved engulfing air. In this situation again, the vertically elongated observation windows 230a, 230b can provide improved observation properties.

As shown in FIG. 24, transparent sheets 231a, 231b are stuck to the windows 230a, 230b, respectively. These sheets 231a, 231b play a roll of preventing the entry of water, for example, from the outside to the inside of the cassette tray 12 through the windows 230a, 230b.

For the sake of reducing a sense of discomfort of the appearance, the transparent sheets 231a, 231b are stuck to the windows 230a, 230b, respectively, being set back from the cover member 12g.

As described above, by forming the observation windows 230a, 230b in the cover member 12g of the cassette tray 12, a user can visually confirm the level 250 of each of the liquids in the chemical liquid bottles 12a, 12b from outside the apparatus body 2. Thus, a user can make certain that the chemical liquids are being injected to the chemical liquid tank 58 from the chemical liquid bottles 12a, 12b.

Fifth Embodiment

Figure 26:
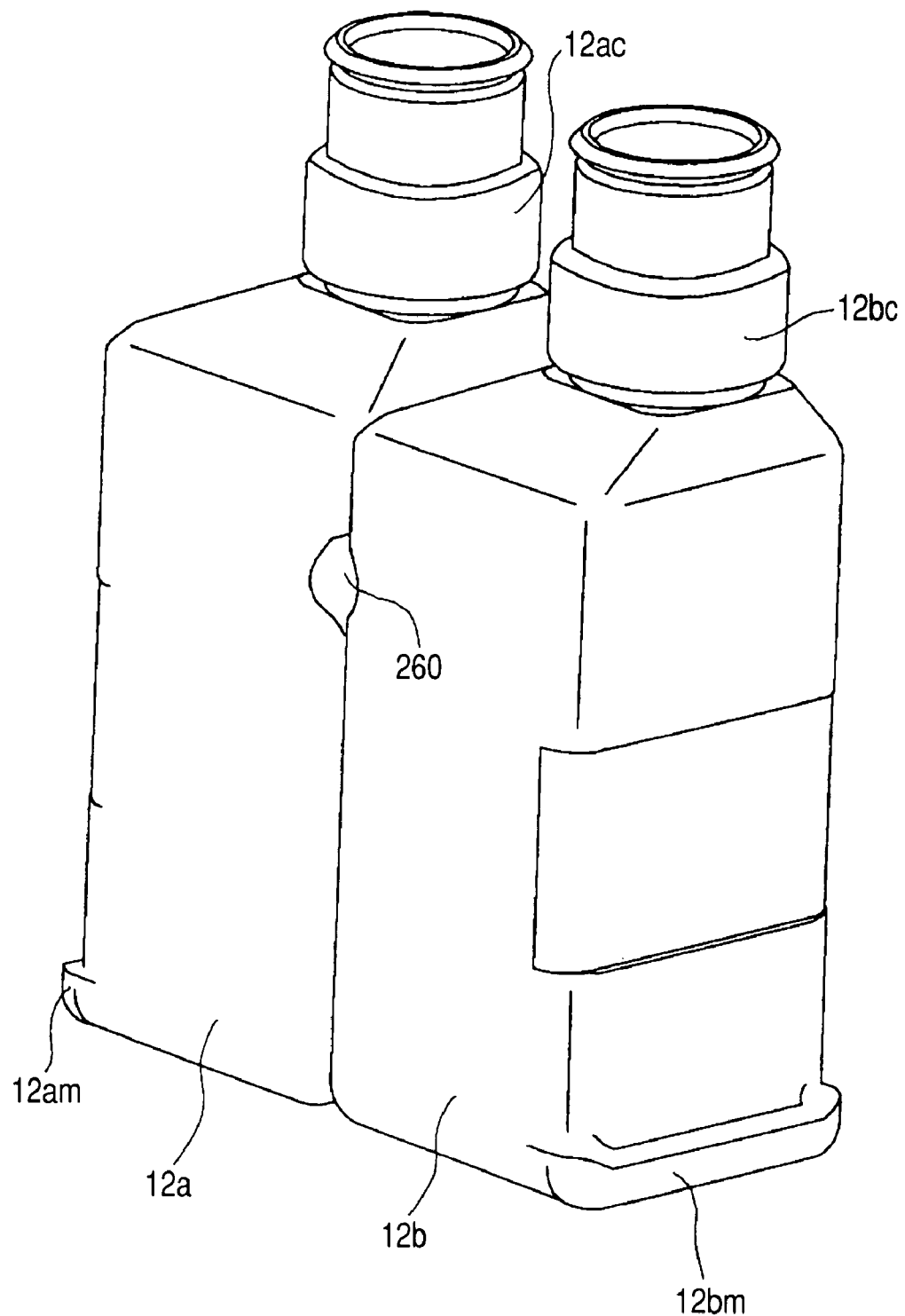
FIG. 26 is an enlarged perspective view illustrating the chemical liquid bottles illustrated in FIG. 1.
Figure 27:
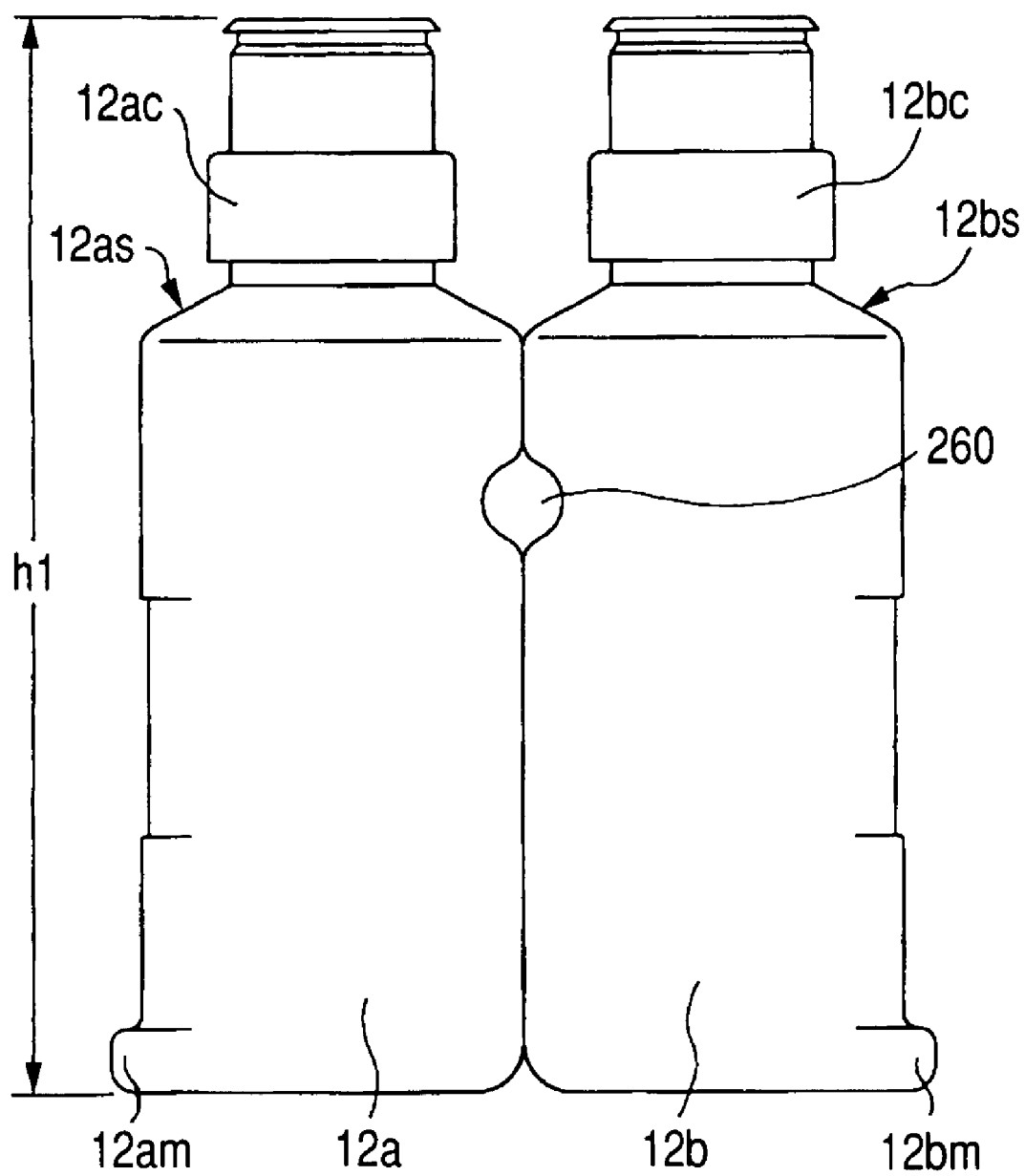
FIG. 27 is a front view illustrating the chemical liquid bottles illustrated in FIG. 26.
Figure 28:
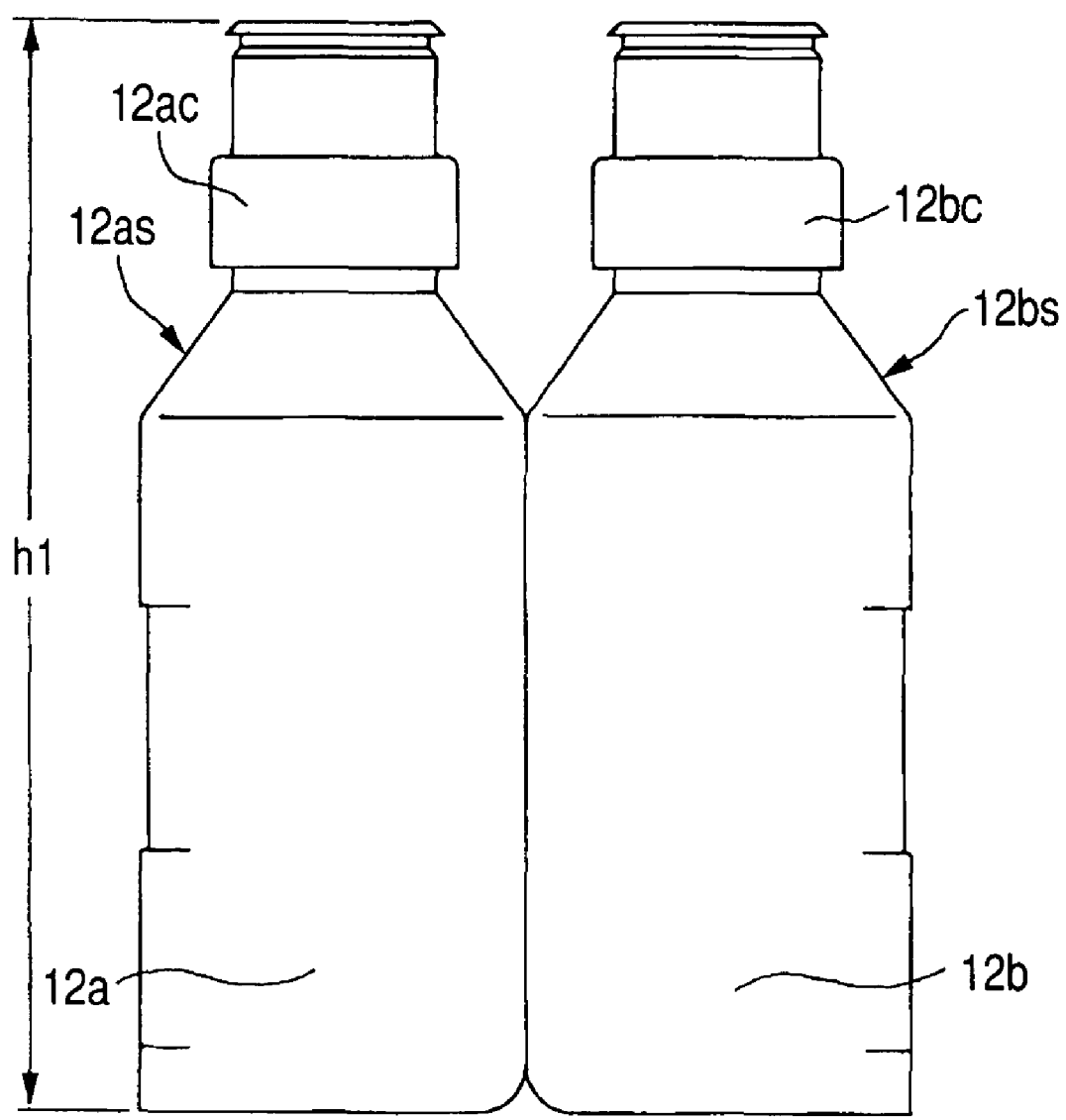
FIG. 28 is a front view illustrating conventional chemical liquid bottles.

With reference to FIGS. 26 to 28, hereinafter is described an endoscope washing/disinfecting apparatus 1 according to a fifth embodiment of the present invention. This embodiment is associated with the prevention of erroneous setting of the chemical liquid bottles at the apparatus.

The disinfecting liquid used in the endoscope washing/disinfecting apparatus 1 of the present invention is obtained by diluting the stock solution of disinfectant in the bottle 12a and the buffer agent in the bottle 12b, in the chemical liquid tank 58 to a predetermined concentration. As shown in FIG. 26, the bottles 12a, 12b are generally bundled together such as by a band so as not to be separated for storage.

In the conventional endoscope washing/disinfecting apparatus, a chemical bottle having a capacity of 750 ml has been used. However, it has been desired to set a larger capacity bottle for larger injection of chemical liquid at the cassette tray 12 without changing the shape of the cassette tray 12.

As shown in FIGS. 26 and 27, the chemical liquid bottles 12a, 12b according to the present invention are each formed in such a way that an inclination of shoulders 12as, 12bs of caps 12ac, 12bc of the bottles 12a, 12b, respectively, are each mitigated as compared with the conventional bottles shown in FIG. 28, while a height h1 of the bottles 12a, 12b remaining unchanged.

In this way, the capacity of each of the bottles 12a, 12b is increased by 25 ml, for example. Thus, the bottles 12a, 12b of large capacity can be set at the cassette tray 12 without changing the shape of the cassette tray 12.

Because the capacity is different between the conventional bottle and the capacity-changed bottle, it is required that the capacity-changed bottle would not be set in the conventional endoscope washing/disinfecting apparatus, or that the conventional bottle would not be set in the endoscope washing/disinfecting apparatus of the present invention.

The possible erroneous setting of the bottles may be prevented, as shown in FIGS. 26 and 27, by providing the projections 12am, 12bm to the bottom faces 12at, 12bt of the bottles 12a, 12b, respectively. Alternatively, the erroneous setting may be prevented by providing an insertion hole 260, as shown in FIG. 27, which is formed between the bottle 12a and the bottle 12b, and by inserting a rod member, not shown, provided in the cassette tray 12 into the insertion hole 260.

Although the description above contains many specificities, these should not be construed as limiting the scope of the invention but as merely providing illustrations of some of the presently preferred embodiments of the present invention. Thus the scope of the present invention should be determined by the appended claims.

What is claimed is:

1. A dewatering method for concurrently washing/disinfecting a plurality of endoscopes each having a plurality of channels of different diameters including a first channel and a second channel and then for concurrently dewatering the plurality of channels of the plurality of endoscopes, the dewatering method comprising:
    a step of continuously supplying high-pressure air for the dewatering to each of the plurality of channels in each of the plurality of endoscopes for a predetermined first period from a plurality of ports supplying the air for the dewatering via one of a plurality of tubes connecting with one of the huts and each of the first and second channels of one of the plurality of endoscopes, and the other of a plurality of tubes connecting with the other of the plurality of ports and each of the first and second channels of the other of the plurality of endoscopes;
    a step of stopping supply of the air to each of the plurality of channels in each of the plurality of endoscopes for a predetermined second period from the plurality of ports via the plurality of tubes by closing a valve;
    a step of repeating a cycle consisting of the supplying step and the stopping step, for a predetermined number of times; and
    the first period and the second period having a predetermined ratio intermittently opening or closing the valve at a predetermined period;
    wherein the predetermined ratio is set based on an air-supplying period necessary to move a droplet in the second channel by continuously supplying the air and an air-stopping period necessary to move the droplet in the first channel by a pressure accompanied with starting supply of the air.

2. The dewatering method according to claim 1, wherein the number of the plurality of ports is two, the number of the plurality of endoscopes is two, the second channel has a larger diameter than the first channel.

3. The dewatering method according to claim 1, wherein the predetermined ratio is set to the first period opening the valve for three seconds and the second period closing the valve for two seconds in succession in each cycle, and the cycle is repeated at least nine times.

4. The dewatering method according to claim 1, wherein the predetermined ratio is set such that the first period opening the valve is set to one second, the second period closing the valve is set to one second, the first and second period making up one cycle, the cycle being repeated at least nine times, after which the cycle is repeated at least nine times, the valve is opened for at least eighteen seconds.

5. The dewatering method according to claim 1, wherein the predetermined ratio is set such that the first period opening the valve is set to one second, the second period closing the valve is set to one second, the first and second period making up one cycle, the cycle being repeated at least five times, after which the one cycle is repeated at least five times, the valve is opened for at least eighteen seconds, and additionally the cycle is repeated at least four times.

* * * * *

UNITED STATES PATENT AND TRADEMARK OFFICE
CERTIFICATE OF CORRECTION

PATENT NO. : 7,824,608 B2
APPLICATION NO. : 11/701846
DATED : November 2, 2010
INVENTOR(S) : Hisashi Kuroshima et al.

Page 1 of 1

It is certified that error appears in the above-identified patent and that said Letters Patent is hereby corrected as shown below:

Column 28, line 40 (claim 1, line 12) Should read:

with one of the plurality of ports and each of the first and second

Signed and Sealed this
Eighth Day of February, 2011

David J. Kappos
*Director of the United States Patent and Trademark Office*